(12) United States Patent
Korpela et al.

(10) Patent No.: US 9,012,201 B2
(45) Date of Patent: Apr. 21, 2015

(54) ENRICHMENT UNIT FOR BIOLOGICAL COMPONENTS AND AN ENRICHMENT METHOD

(75) Inventors: Matti Korpela, Naantali (FI); Tytti Miettinen, Turku (FI); Tuija Tenhunen, Lielahti TL (FI); Teemu Korpimäki, Turku (FI); Pekka Mattsson, Turku (FI); Mika Tuomola, Littuinen (FI)

(73) Assignee: BioControl Systems, Inc., Bellevue, WA (US)

( * ) Notice: Subject to any disclaimer, the term of this patent is extended or adjusted under 35 U.S.C. 154(b) by 1573 days.

(21) Appl. No.: 12/085,898

(22) PCT Filed: Dec. 4, 2006

(86) PCT No.: PCT/FI2006/000403
§ 371 (c)(1),
(2), (4) Date: May 28, 2009

(87) PCT Pub. No.: WO2007/063174
PCT Pub. Date: Jun. 7, 2007

(65) Prior Publication Data
US 2009/0311733 A1 Dec. 17, 2009

(30) Foreign Application Priority Data

Dec. 2, 2005 (FI) .................................. 20051248

(51) Int. Cl.
| | |
|---|---|
| *C12N 1/02* | (2006.01) |
| *G01N 33/543* | (2006.01) |
| *B03C 1/01* | (2006.01) |
| *B03C 1/28* | (2006.01) |
| *C12M 1/00* | (2006.01) |

(Continued)

(52) U.S. Cl.
CPC ............ *G01N 33/54326* (2013.01); *B03C 1/01* (2013.01); *B03C 1/286* (2013.01); *C12M 47/02* (2013.01); *C12M 47/04* (2013.01); *G01N 1/40* (2013.01); *G01N 35/0098* (2013.01)

(58) Field of Classification Search
None
See application file for complete search history.

(56) References Cited

U.S. PATENT DOCUMENTS 4,710,472 A * 12/1987 Saur et al. .................. 435/308.1
5,647,994 A    7/1997 Tuunanen et al.
(Continued)

FOREIGN PATENT DOCUMENTS

EP        787296        3/2001
FI   WO 99/42832   *  8/1999 ........... G01N 33/543
(Continued)

*Primary Examiner* — Chris L Chin
*Assistant Examiner* — Richard Moerschell

(57) ABSTRACT

A biological component enrichment unit for the isolation, purification and/or determination of a biological component using particles (3) and/or another solid phase, which enrichment unit comprises at least one sample container (1, 15, 26, 32, 39) for the realization of the biological sample method. The enrichment unit comprises a lead-through structure (5), such as a bushing (21, 27) made up of one or several parts or a cover having one or several openings (25, 36). The lead-through structure and one or several sample containers can be brought into connection with one another so that, when the lead-through structure is placed on top of the sample container, a functional unit is formed for the realization of the biological method, such as for the binding of the component, the growing, isolation, purification, enrichment of the bacteria or cell or for another similar method.

18 Claims, 23 Drawing Sheets

(51) Int. Cl.
  *G01N 1/40* (2006.01)
  *G01N 35/00* (2006.01)

(56) References Cited

U.S. PATENT DOCUMENTS

| | | |
|---|---|---|
| 5,834,197 A | 11/1998 | Parton |
| 5,837,144 A | 11/1998 | Biennhaus et al. |
| 5,942,124 A | 8/1999 | Tuunanen |
| 6,020,211 A | 2/2000 | Tuunanen |
| 6,065,605 A | 5/2000 | Korpela et al. |
| 6,143,577 A | 11/2000 | Bisconte Sconte De Saint Julien |
| 6,159,689 A | 12/2000 | Parton |
| 6,207,463 B1 | 3/2001 | Tuunanen |
| 6,723,237 B1 | 4/2004 | Tajima |
| 2003/0008389 A1* | 1/2003 | Carll ................. 435/302.1 |
| 2005/0048033 A1* | 3/2005 | Fraser et al. ............ 424/93.7 |

FOREIGN PATENT DOCUMENTS

| | | | | |
|---|---|---|---|---|
| FI | WO 2004/035217 | * | 4/2004 | ........ B03C 1/28 |
| WO | 8705536 | | 9/1987 | |
| WO | 9004019 | | 4/1990 | |
| WO | 9612960 | | 5/1996 | |
| WO | 9942832 | | 8/1999 | |
| WO | 2004035217 | | 4/2004 | |
| WO | WO 2004/035217 | * | 4/2004 | ........ B03C 1/28 |
| WO | 2005037440 | | 4/2005 | |

* cited by examiner

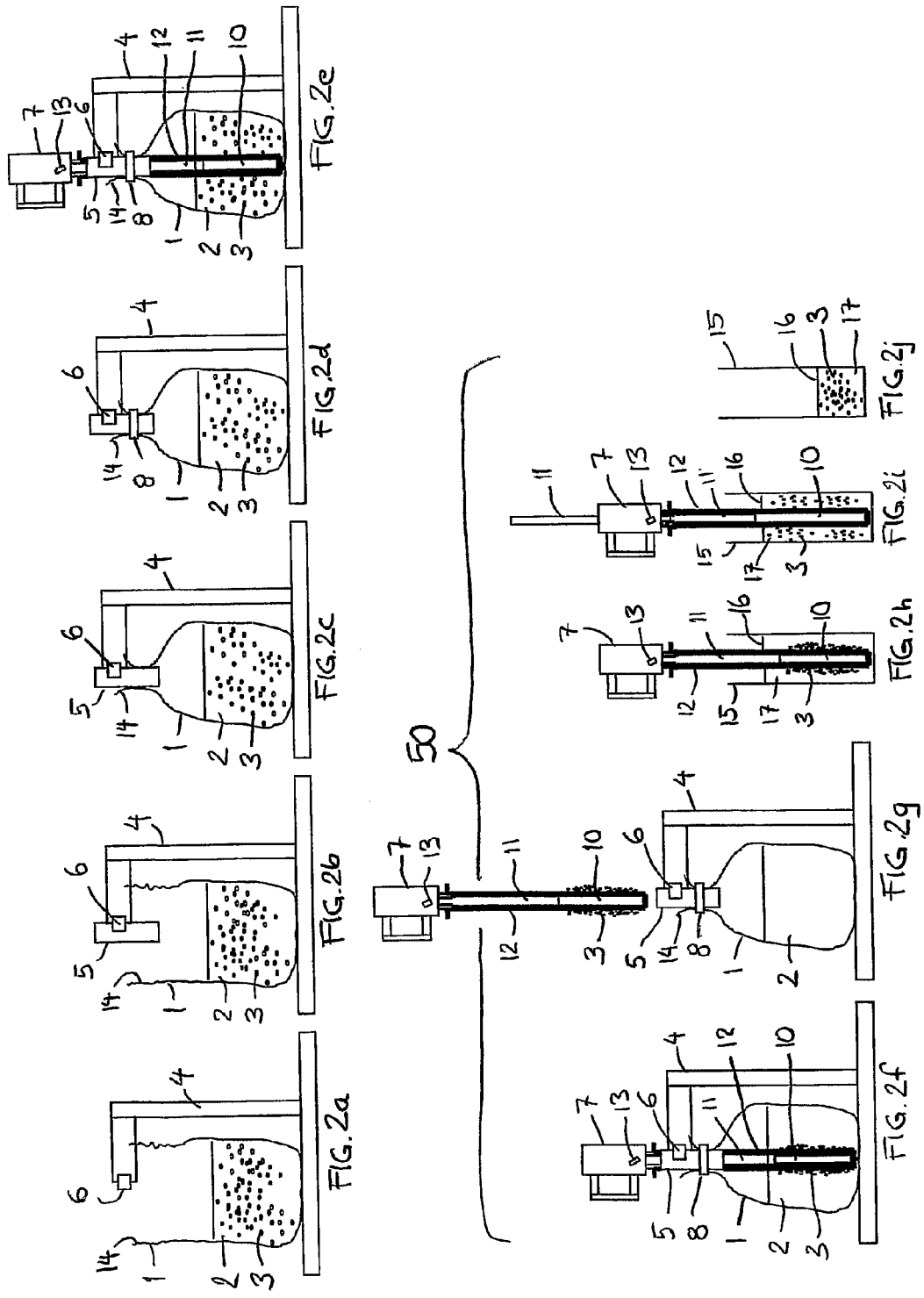

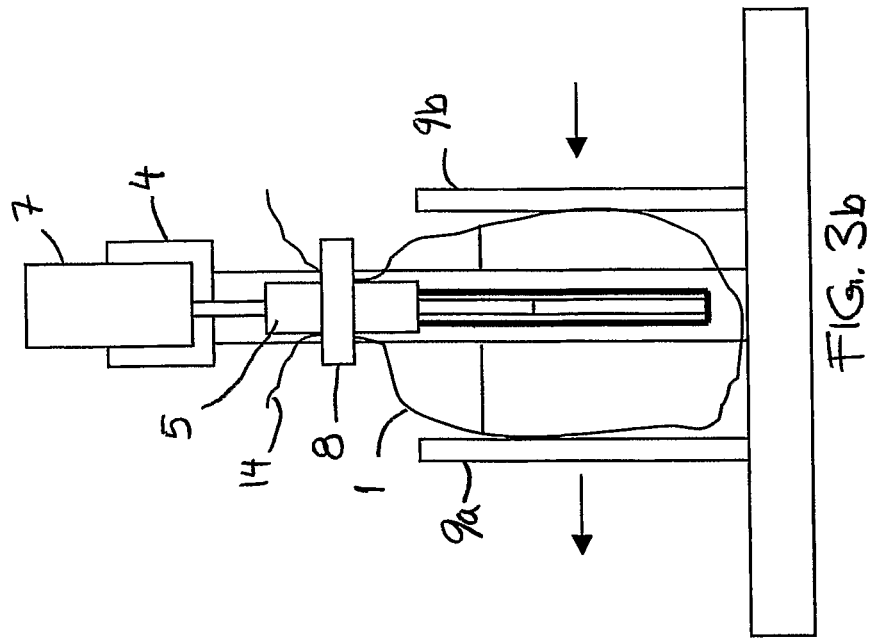
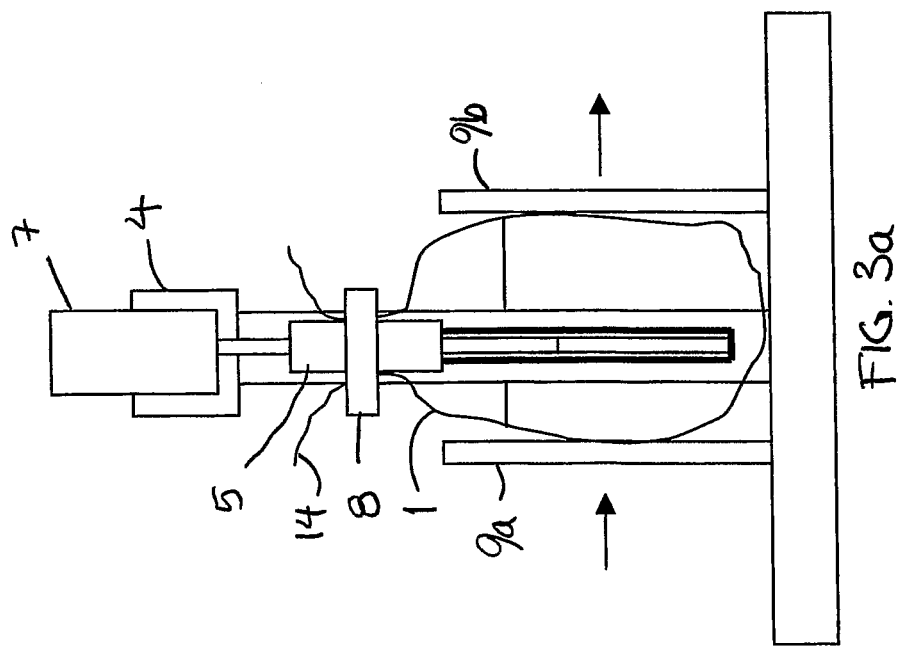

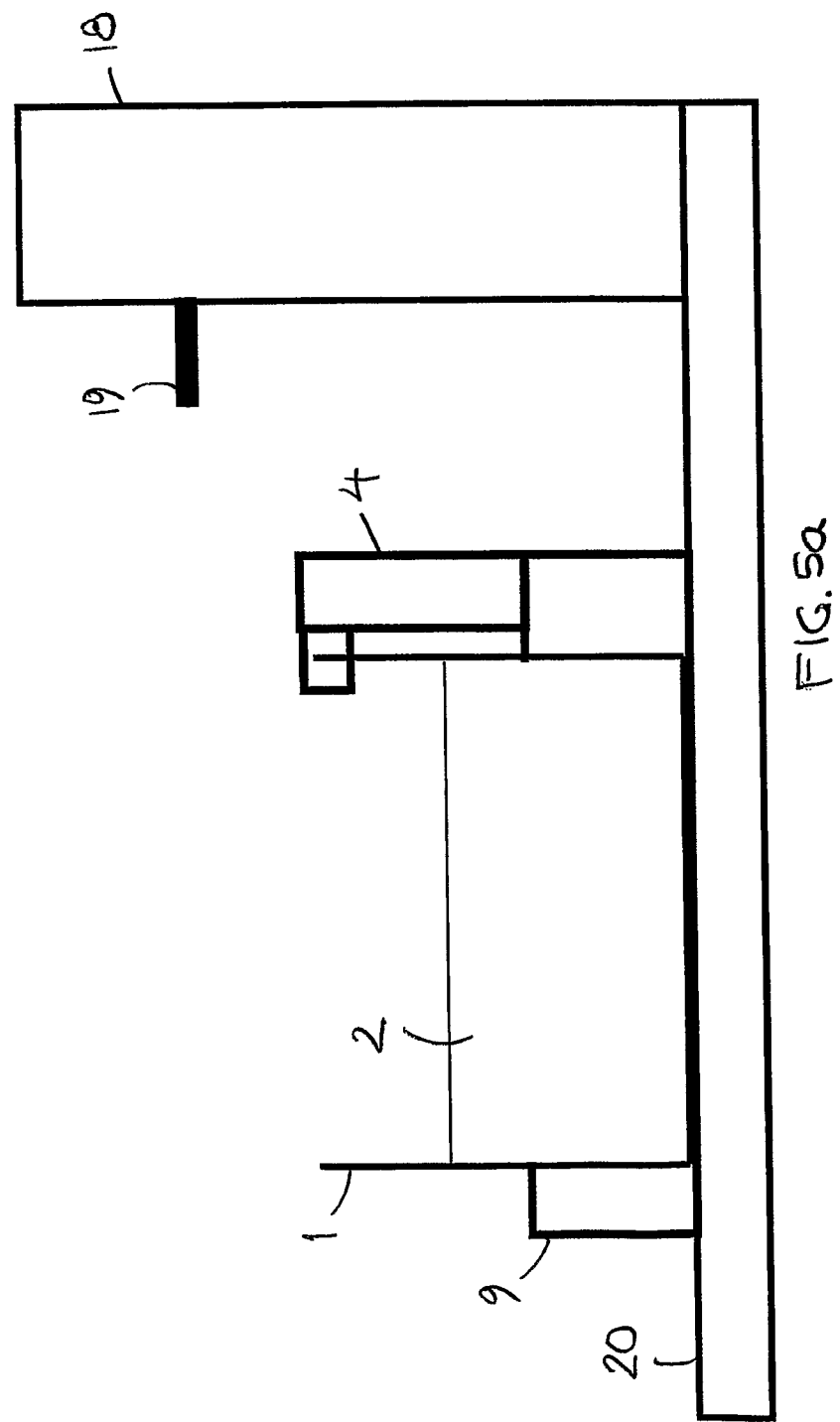

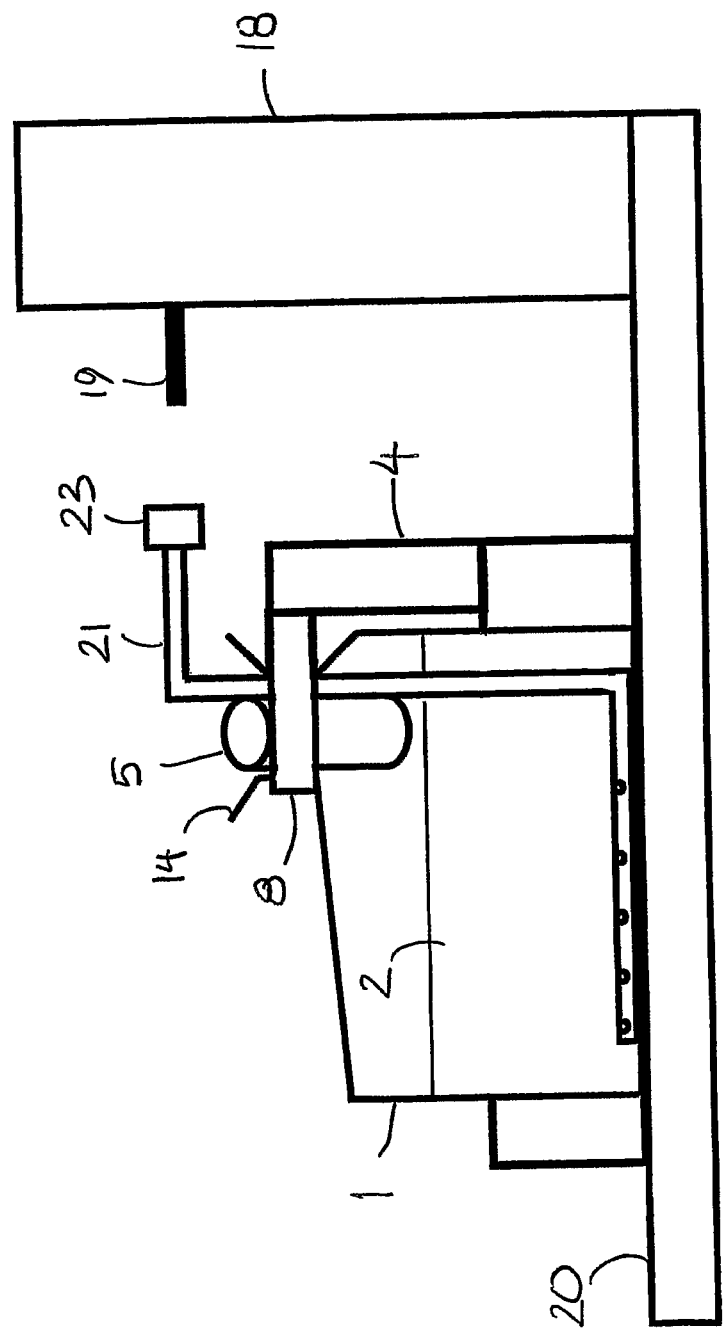

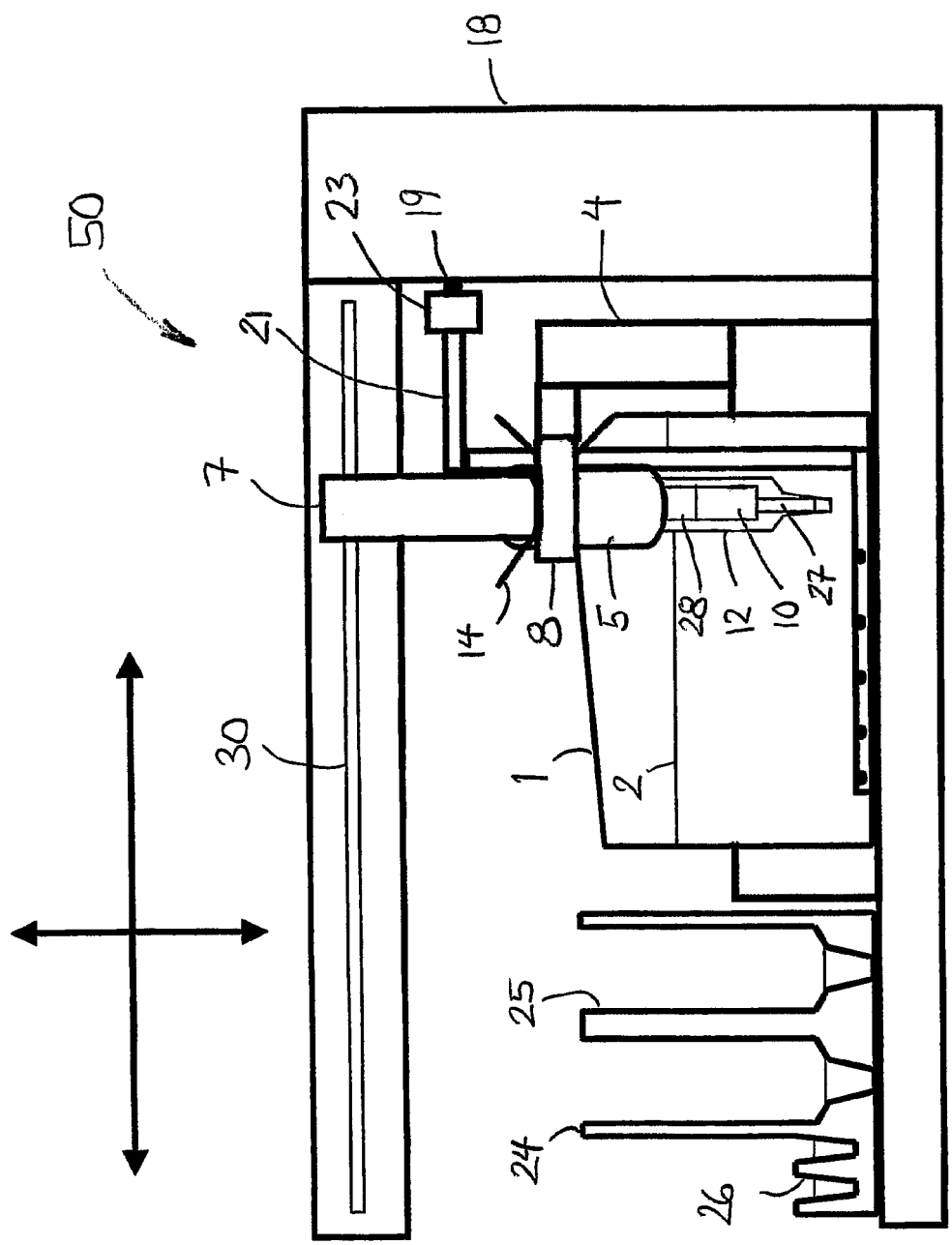

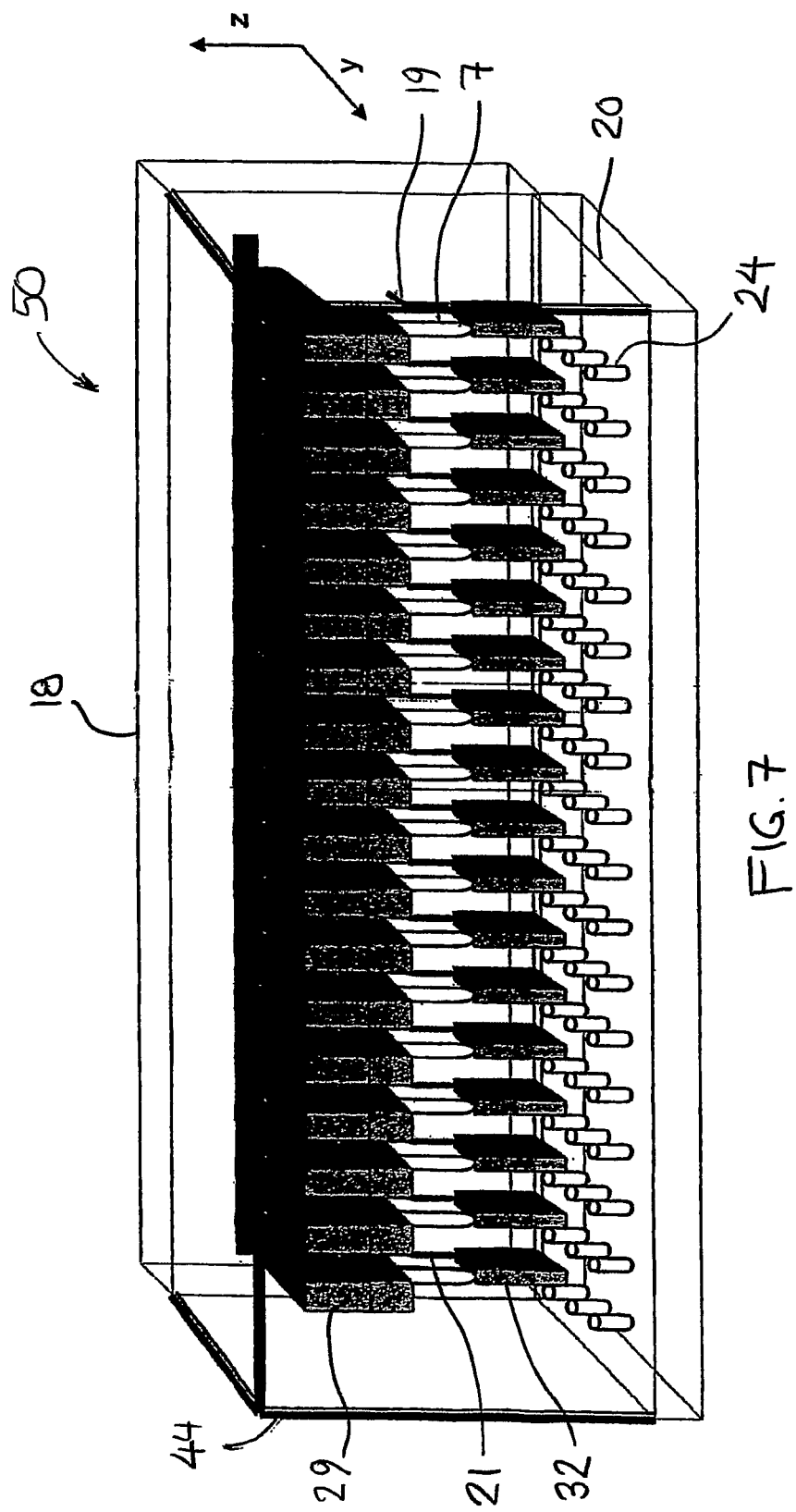

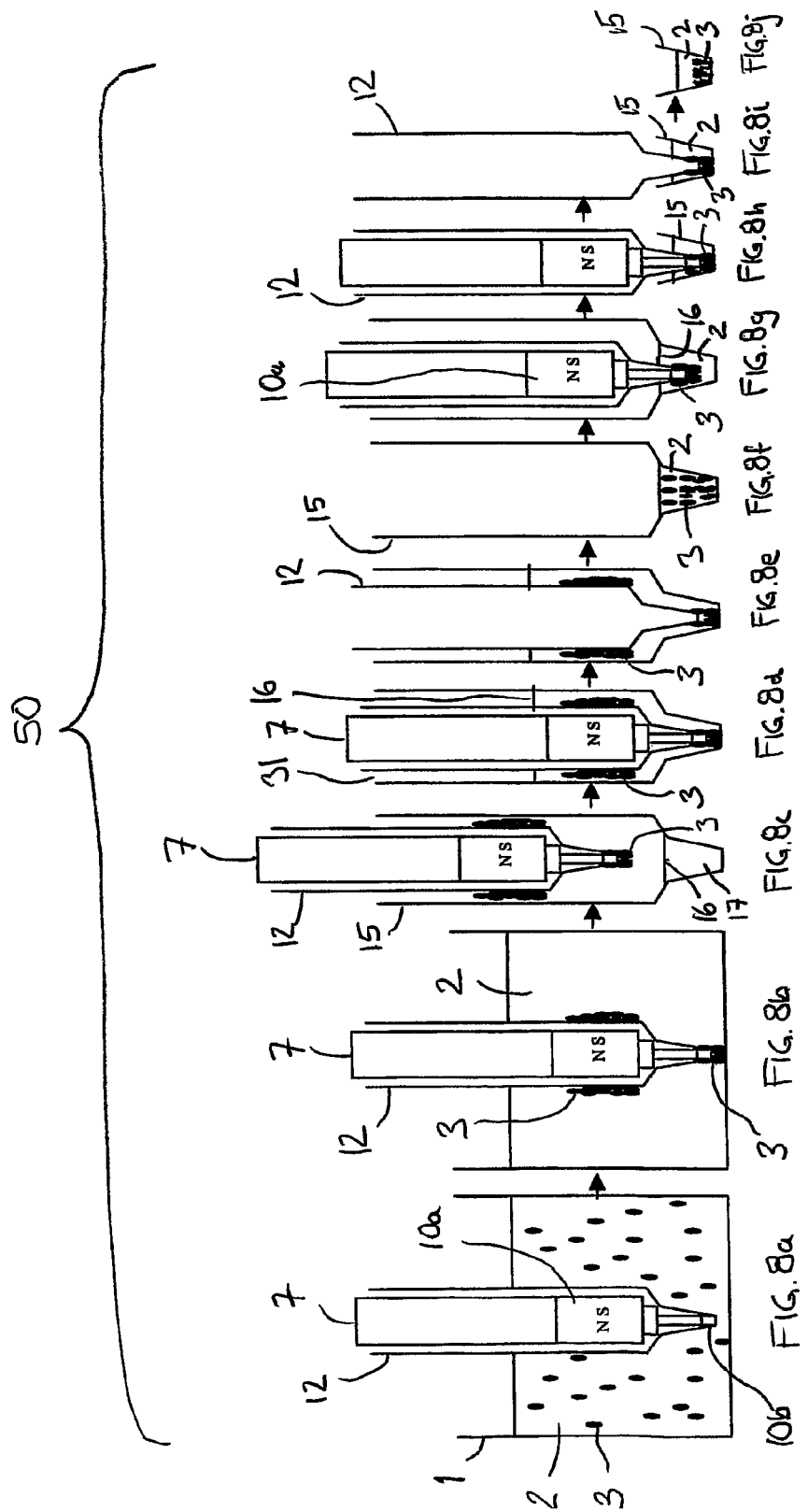

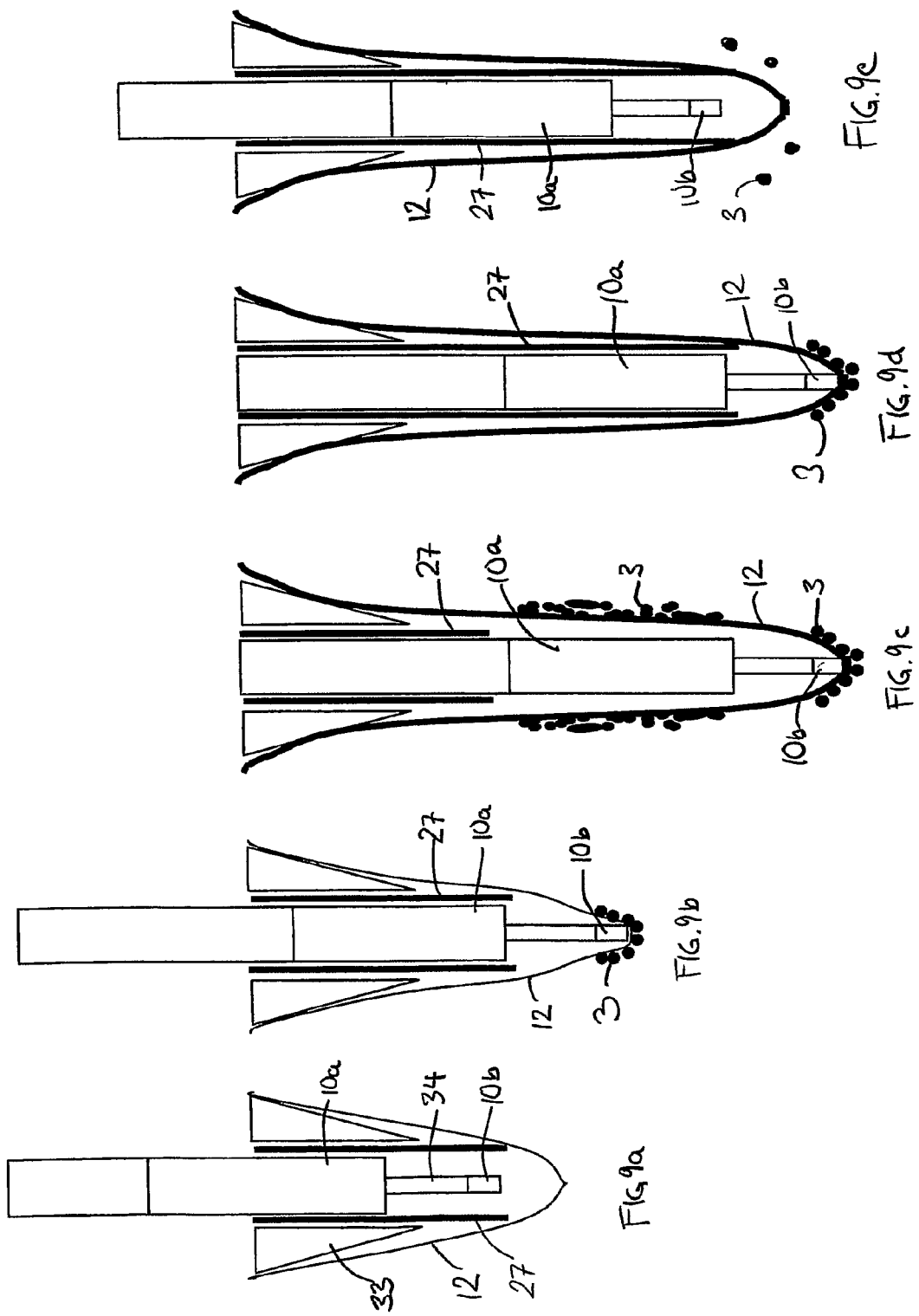

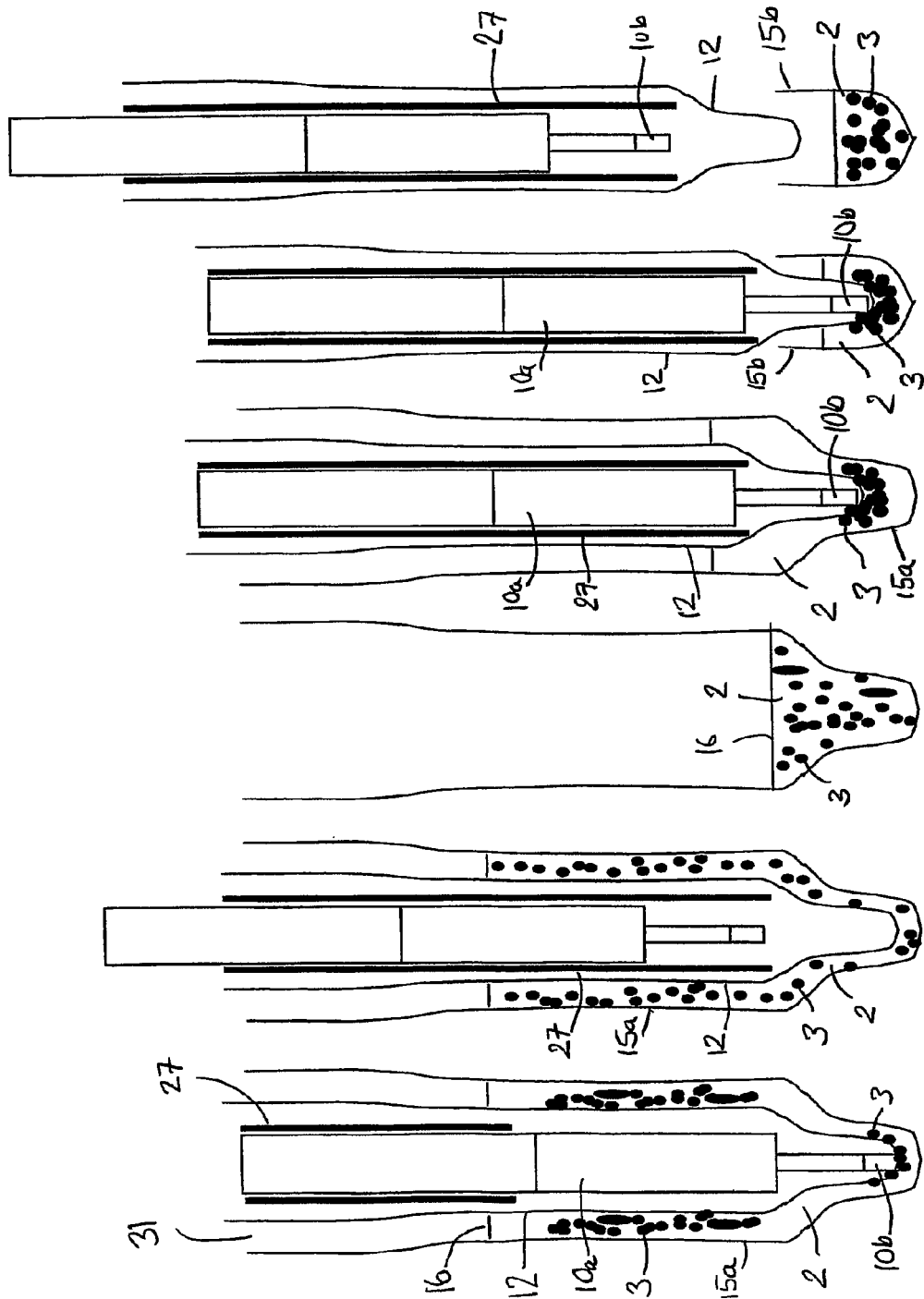

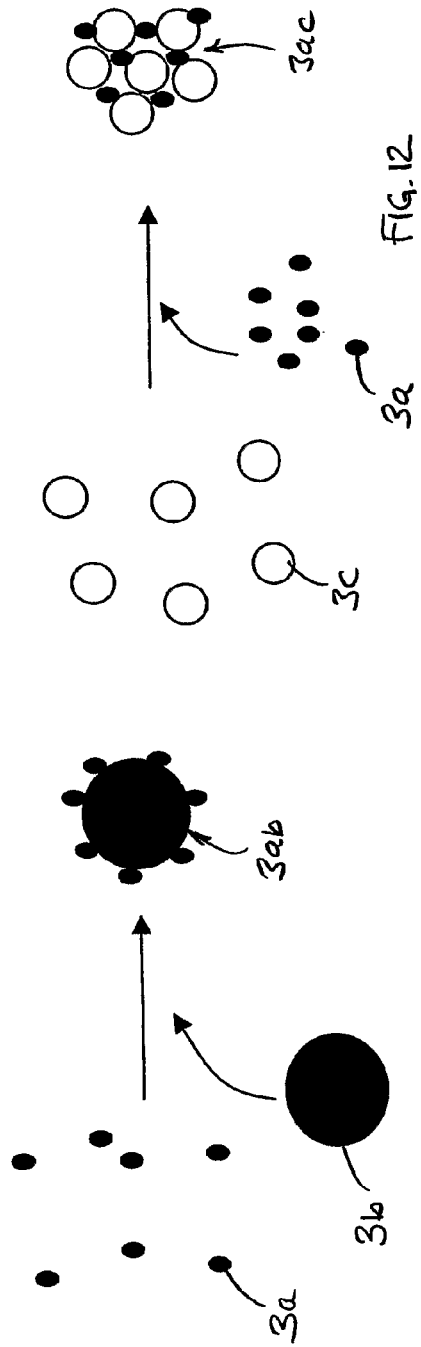

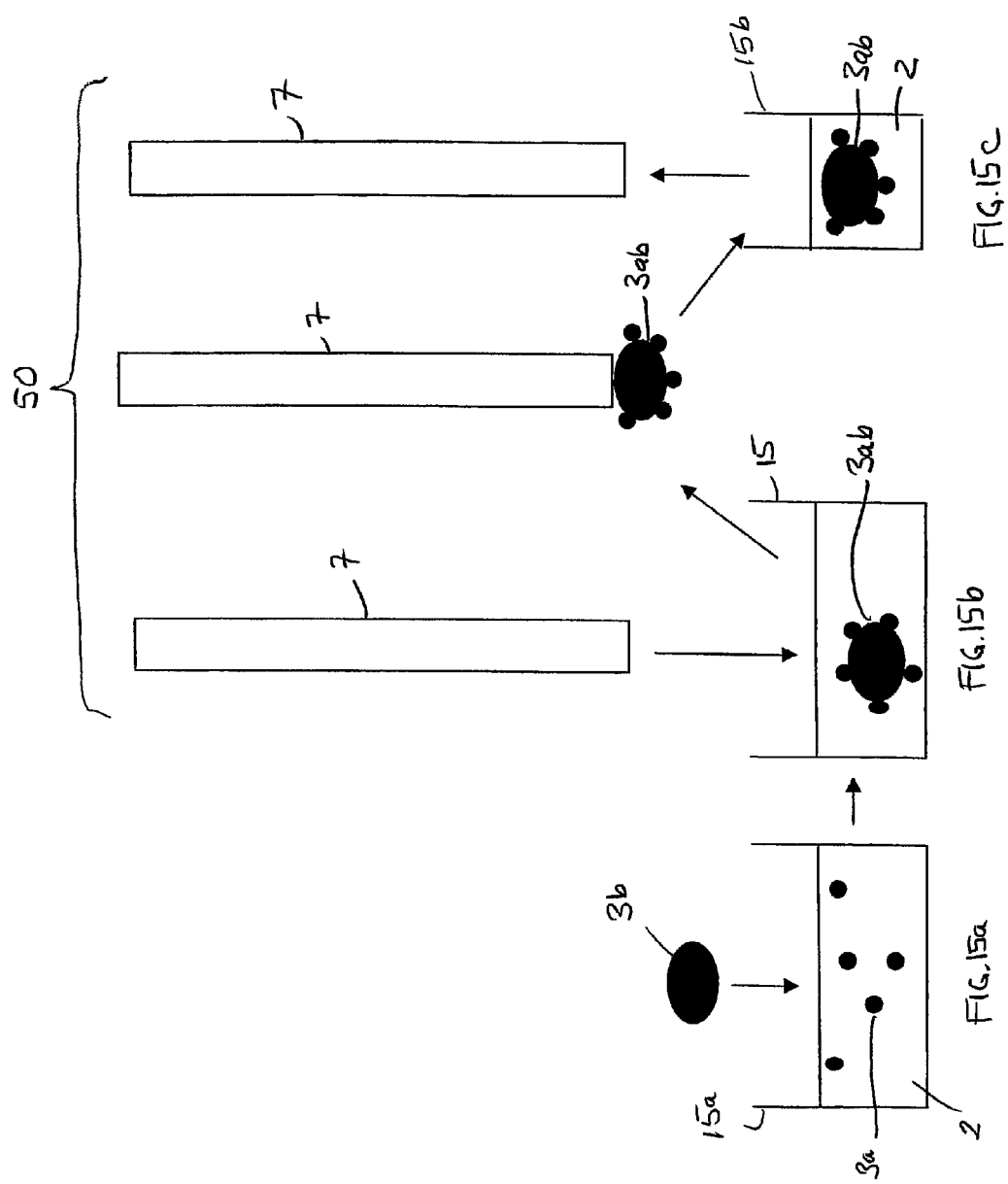

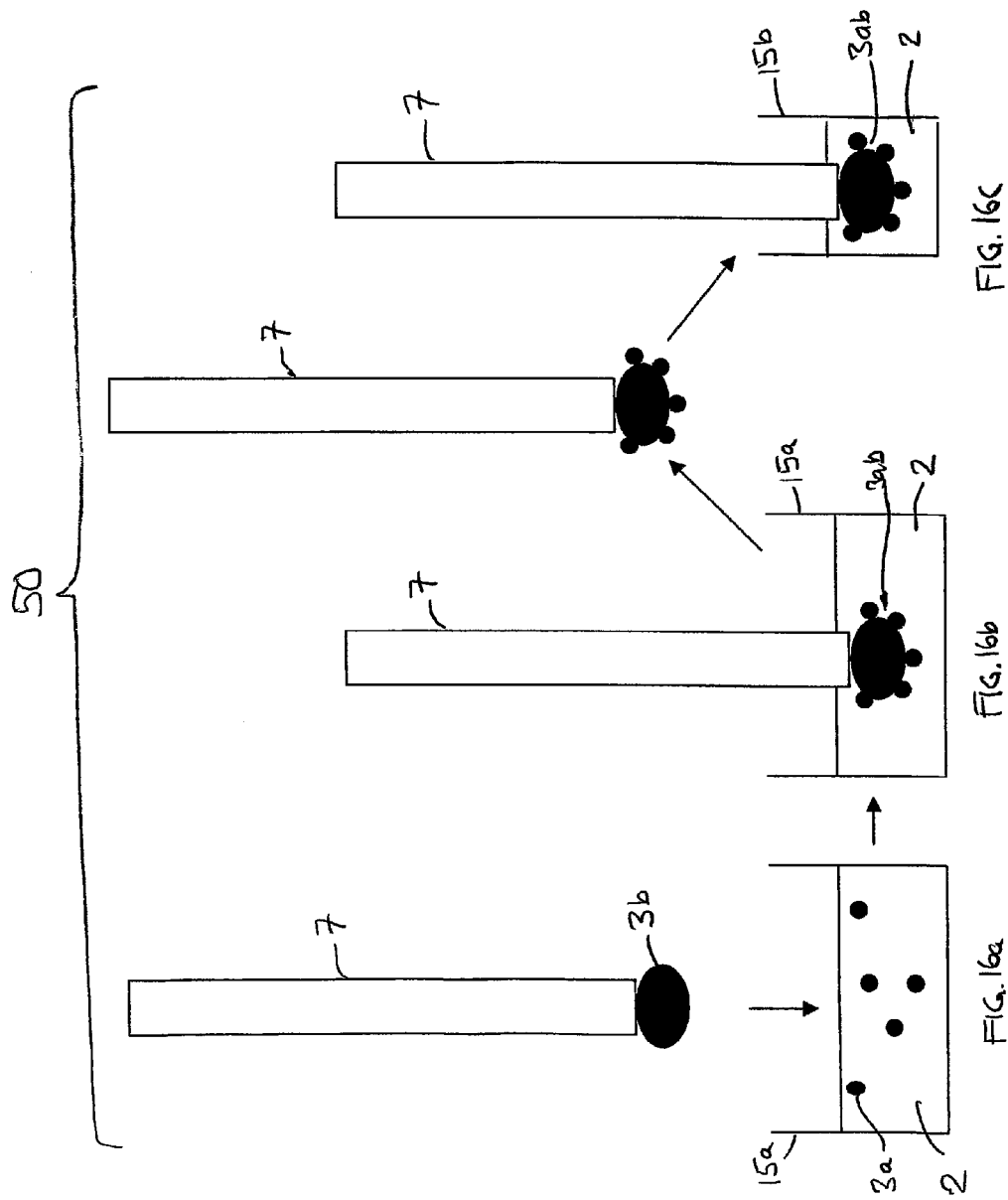

ENRICHMENT UNIT FOR BIOLOGICAL COMPONENTS AND AN ENRICHMENT METHOD

This application is a 371 of international application PCT/FI2006/000403 filed Dec. 4, 2006, which claims priority based on Finnish patent application No. 20051248 filed Dec. 2, 2005, which is incorporated herein by reference.

OBJECT OF THE INVENTION

The object of the invention is enrichment and a biological component enrichment unit for the isolation, purification and/or determination of a biological component using particles and/or another solid phase. The apparatus according to the invention can also be used to grow bacteria and cells. The biological component enrichment unit refers to a set of apparatuses suitable for the growing, isolation, purification, enrichment and determination of bacteria, viruses, proteins and nucleic acids. The object of the invention is also concentration and an apparatus for the concentration of biological components from a liquid sample using the particles contained in a solution so that the sample is concentrated from a large solution volume to a small solution volume. In this context, enrichment and concentration can be regarded as similar operations for bringing a sample from a large volume to a small volume.

BACKGROUND OF THE INVENTION

The following is a description of concepts relating to the field of the invention and a more detailed specification of their meaning.

The biological component enrichment unit refers to a set of apparatuses suitable for the growing, isolation, purification, enrichment and determination of bacteria, viruses, proteins and nucleic acids.

Particles or magnetic particles refer to all objects that can be moved by means of magnetism, directly or by linking them with a material to be magnetised. Many different particles are known to be movable by means of a magnet, and the applications in which they are used also vary greatly. The size of the particles used in e.g. microbiology ranges from 0.01 to 100 μm, and most typically from 0.05 to 10 μm. Such particles include e.g. particles containing ferromagnetic, paramagnetic or superparamagnetic material. The particles may also be magnetic in themselves, in which case they can be moved by means of any ferromagnetic object.

The magnetic tool or apparatus intended for handling the particles has an element that uses magnetism, hereinafter referred to as a magnet. It may be a permanent magnet or an electromagnet that attracts magnetisable or magnetic particles. Usually, the magnet is most preferably a round bar magnet. It may also be an object of another shape. The magnet may also be comprised of one or several objects, such as magnets or ferromagnetic objects.

The magnet must be overlaid with a protective membrane or coating that protects the magnet from harmful conditions and enables the handling, such as binding and release, of the particles. The structure of the protective membrane may vary greatly and it may be, e.g., a thin film of flexible or stretchable material or a protection that is made, say, from rigid plastic.

Particles are generally used as solid phases for binding various kinds of biological components, such as nucleic acids, proteins, bacteria or cells. The effective enrichment of e.g. pathogenic bacteria from a large to a small sample volume is a critical factor, as it directly influences the sensitivity and analysis time of bacterial determination.

No sufficiently efficient method is currently available for concentrating biological components by means of particles from a large volume to a small volume.

PRIOR ART

Many problems are encountered when the aim is to collect biological components from a large sample volume and to concentrate the collected biological components to a significantly smaller volume. Different kinds of filters and strainers are currently used, through which the sample can be run. The use of filters or strainers is particularly problematic in cases where the desired biological component is contained in a sample containing a very large amount of particulate impurities. Filters and strainers easily get clogged.

Magnetic particles are an interesting alternative for handling problematic biological sample materials, as the magnet particles can be separated from the rest of the sample by means of a magnetic field. When handling large sample volumes, the use of magnetic particles also involves major problems. I. D. Odgen et al (Letters in Applied Microbiology, 2000, 31, 338-341) stated that 10 ml is the largest possible sample volume that can be used in handling magnetic particles using a conventional external magnet. In their study *Escherichia coli* O157, they isolated bacteria with magnetic particles that were coated with specific antibodies. They found that the apparatuses used to isolate magnetic particles are a bottleneck where large sample volumes are used in food diagnostic applications.

In the Pathatrix system of Matrix MicroScience Ltd., antibody-coated magnetic particles are circulated from a food sample stomacher bag, by means of a hose pump, past a magnet located outside the stomacher bag. The magnet is located in the bend of the sample-circulating hose connected to the hose pump, to which bend the magnetic particles and the bacteria collected on the surface of the particles are bound. Once the sample has been circulated with the pump for a sufficient time, the circulation of the sample in the hose is discontinued. The method requires a lot of manual work to eventually transfer the magnetic particles from inside the hose into the desired tube. The method is labour-intensive and the simultaneous handling of several samples requires a great deal of space and a plurality of peripheral apparatuses.

Several patent publications describe the use of magnetic particles for handling large sample volumes. Many of these patent publications discuss the use of liquid flows for moving the magnetic particles past the magnet located outside the sample container/hose/pipette tip: U.S. Pat. No. 5,647,994 (Tuunanen et al.), U.S. Pat. No. 5,834,197 (Parton), U.S. Pat. No. 6,143,577 (Bisconte Sconte De Saint Julien), U.S. Pat. No. 6,159,689 (Parton), and U.S. Pat. No. 6,723,237 (Tajima). Methods for collecting magnetic particles from the sample container and concentrating them to small solution volumes using special magnetic tools are also described in several publications, for example: U.S. Pat. No. 6,065,605 (Korpela et al.), U.S. Pat. No. 6,020,211 (Tuunanen), U.S. Pat. No. 5,942,124 (Tuunanen) and WO2005037440 (Korpela et al.). Patent application WO2005037440 also describes a special reactor unit e.g. for the growing of bacteria, and for the collection and concentration of magnetic particles from the sample.

Application publication WO 87/05536 (Schröder) describes the use of a permanent magnet that is movable inside a plastic protection for collecting ferromagnetic material from a solution containing such material. When the magnet is in the lower position, the ferromagnetic material gathers in the end portion of the magnet unit. The publication describes the transfer of the collected ferromagnetic material and the release of the material from the end portion into the solution contained in another container. The release of the ferromagnetic material is described as being effected by the design of the plastic protection, which prevents the material from moving when the magnet is moved upwards.

Patent publication U.S. Pat. No. 5,837,144 (Bienhaus et al.) describes a method for collecting particles by means of a special magnet equipped with a plastic protection. This publication describes the binding of particles from a solution which is taken away from the container by means of various arrangements. By moving the magnet, the particles can be released from the top of the protective membrane.

Publication U.S. Pat. No. 5,942,124 (Tuunanen) describes an apparatus with which the particles can be concentrated into the very end portion of the magnet unit. Publication U.S. Pat. No. 6,020,211 (Tuunanen) describes the use of the apparatus described in the preceding publication together with the so-called conventional large magnet technology. Publication U.S. Pat. No. 6,065,605 (Korpela et al.) takes the application of the solution described in the publication U.S. Pat. No. 5,942,124 (Tuunanen) further for the handling of relatively large volumes. The publication describes a method in which the particles have first been collected by means of a special magnet unit containing a large magnet. After this, the magnet unit described in publication U.S. Pat. No. 5,942,124 (Tuunanen) is used to transfer the particle pellet on into smaller containers. Publication U.S. Pat. No. 6,207,463 (Tuunanen) similarly applies the above-described magnet unit, which can be used to collect particles into the very end portion of the apparatus.

The methods described in particular in publications U.S. Pat. No. 5,942,124 (Tuunanen), U.S. Pat. No. 6,020,211 (Tuunanen), U.S. Pat. No. 6,065,605 (Korpela et al.), U.S. Pat. No. 6,207,463 (Tuunanen) and EP 0787296 (Tuunanen), intended for collecting particles using a very small magnet, are impractical. It is slow and inefficient to use a small magnet in the magnetic tool when collecting particles from a large solution volume.

No publication describes a solution that would allow for the possibility of using very different sample containers for the growing of bacteria/cells, the collection of particles from a large sample volume, the efficient washing of the particles and for concentration. When the aim is to collect a limited number of biological components from a large volume, e.g. for their determination, an efficient/powerful method is needed to collect the magnetic particles from the sample. On the other hand, it must be possible to concentrate the collected magnetic particles to a small volume. No publication describes the solution according to the invention, which consists in bringing the particles on the same protective membrane from a large volume to a very small container, where the biological components may be determined using various methods of determination.

PURPOSE OF THE INVENTION

The purpose of the invention is also to provide a biological component enrichment unit that is better and more efficient than known apparatuses. Furthermore, the purpose of the invention is to eliminate the shortcomings of the solutions according to the prior art as described above.

Characteristics of the Enrichment Unit According to the Invention

The enrichment unit according to the invention has a special lead-through structure or bushing, the use of which makes it possible to form a functional unit for binding the biological component and for isolating it from the sample material with the help of a solid phase. The lead-through structure may be such that can be fastened to the sample container with a special locking mechanism, or it may simply be placed on top of the sample container. When the sample container is such that it does not easily stay in an upright position, the lead-through structure can be used to fasten the sample container to a special stand, which provides effective support for the sample container. The lead-through structure and the stand in accordance with the invention can be of one and the same structure, or the lead-through can be such that it can be fastened to the stand. Food sample stomacher bags, water sample bags and blood bags are examples of containers that can well be supported using the method in accordance with the invention. The lead-through structure according to the invention enables the provision of an opening for introducing various solutions and particulate materials into the sample. The sample material may also be introduced into the sample bag through the lead-through structure described in the invention. The lead-through structure is also effective for reducing splashes, evaporation and cross-contaminations, which is a very important issue, in particular when using the method for diagnostic or analytical applications.

The lead-through structure can have one or several separate openings, and the openings can be closed, as needed, e.g. with a plug, membrane, filter or other suitable structure. Through the lead-through structure according to the invention, various apparatuses can be introduced into the sample contained in the sample container, e.g. to provide aeration and agitation. The lead-through structure according to the invention also serves as a path to introduce a suitable solid phase into the sample container and to transfer the solid phase away from the sample container. If the solid phases used are particles that are magnetic in themselves or magnetisable, the lead-through structure also serves as a stand for holding the magnetic tool while the tool is collecting particles from the sample. The solid phase can also be part of the magnetic tool or other tool having a suitably arranged area for collecting the desired biological component from the sample. The tool can be a structure where, e.g., antibodies or other affinity ligands are attached to the surface of the structure for collecting one or several desired biological components from the sample. One of the embodiments of the invention is a coated rod or dipstick type solution.

The lead-through structure can advantageously be arranged so that several lead-through structures are an integral part of or can be fastened to the same stand. Such a stand may also be part of an automatic apparatus. The apparatuses or components relating to the aeration and agitation arranged through the lead-through structure may also be part of an automatic apparatus.

The enrichment unit according to the invention is a set of apparatuses, which is suitable for the growing of bacteria and different kinds of cells, and which can also be used to isolate, purify, enrich and determine various biological components from large samples. The biological components may be e.g. proteins, peptides, nucleic acids, viruses, bacteria, yeasts, parasites, cells, cell organelles, allergens, toxins or hormones. The biological components can be bound to the surface of particles or special rods and, when bound to the said surfaces, they can be washed, concentrated, and their presence and/or amount can be determined quantitatively. The invention can be applied, in particular, in food diagnostics for the enrichment of pathogenic bacteria from food samples, and other applications including the isolation, purification and determination of e.g. cells, parasites, cell organelles, viruses, toxins, allergens, proteins and nucleic acids.

With the enrichment unit, the desired biological component can be collected from a large volume to a significantly smaller volume and, when needed, the concentration of the component in the sample can be determined.

The enrichment unit according to the invention is characterised in that the equipment includes a special lead-through structure, into which the magnetic tool used for handling the particles can be introduced while the particles are collected. The lead-through structure is used on top of a suitable sample container or in connection therewith. The lead-through structure has many purposes, the most important of which are to prevent evaporation, to eliminate cross-contamination of different samples, to provide an opening for introducing solutions and particles, to provide an opening for introducing samples, to prevent sample splashes, to hold the magnetic tool, to hold other peripheral apparatuses, and in the case of toxic and pathogenic samples in particular, the lead-through structure can be used to facilitate sample disposal. The lead-through structure can have a special, rigid cover-like structure that can incorporate a suitable number of openings for one or several magnetic tools. The lead-through structure can also have openings for the sets of apparatuses needed for the aeration and/or agitation of the sample. The lead-through structure can also be comprised of an assembly in which the cover is a stand-alone structure and in which the sample container can be placed.

The lead-through structure can also be comprised of more than one piece. The same lead-through structure can also be used with several different sample containers. In this case, the lead-through structure isolates the samples efficiently from one another. Specific bulges or recesses can be provided under the lead-through structure, the effect of which bulges or recesses can be e.g. to delimit different sample compartments and facilitate the handling of the magnetic tool. The lead-through structure may be comprised of a suitable ring-, tube-, bushing- or other support structure together with the sample container. The lead-through structure may be fastened as a fixed part, with a special locking mechanism, to the sample container, or the lead-through structure may be arranged in connection with the sample container without any special locking mechanism. The lead-through structure may be e.g. of plastic, glass, aluminium or other ferromagnetic or non-ferromagnetic material. The material of the lead-through structure is preferably autoclavable plastic material, such as e.g. polypropylene or aluminium.

Various tubes, sample plates, decanter glasses, stomacher bags or other containers can serve as sample containers. The sample container can have closed compartments for several different samples. With the help of the lead-through structure, a magnetic tool, the equipment needed for aeration, equipment needed for arranging the agitation and other equipment can be introduced into the sample container. One or several magnetic tools can be introduced into the same sample as required. The agitation of the sample contained in the sample container may also be arranged using an external agitator, or the magnetic tool may be used to agitate the sample. When the sample container is a bag, such as a food sample stomacher bag, it is preferable to arrange the lead-through structure using a special tube/bushing arrangement. As a bag does not readily remain in the upright position by itself, it is not possible to attach a lead-through structure to it and to place a magnetic tool in it to collect particles from the bag.

One of the lead-through solutions according to the invention requires the sample container, the bag, to be fastened around the tube/bushing arrangement. The tube/bushing arrangement may be an integral part of a special stand that supports the bag. The tube/bushing arrangement may also be a separate object and, if required, even a disposable consumable. In diagnostic applications in particular, disposability is an important issue. Such an arrangement provides a stable and sufficiently rigid arrangement for introducing into the bag the magnetic tool and any other means relating to the arrangement of aeration/agitation.

According to one embodiment, the function of the lead-through structure as explained above may be achieved entirely by using structures located outside the bag. In this case, special structures may support the bag, and the structures may have a special adhesive or other fastening element for fastening the bag to the structures from the outer edges of the bag. As the structures are movable, the bag may be opened and closed as desired. The structures may be such that they can be shaped further if required or have originally pre-shaped areas, for example for placing the magnetic tool on the bag or for introducing various peripheral apparatuses into the bag. This solution enables savings in consumables, as the structures, being located outside the bag, are not contaminated nor do they need to be changed when changing the bag.

The structures described above may also have special disposable structures, the purpose of which is, for example, to give additional support when holding e.g. the magnetic tool standing in the bag during particle collection. In the case of a bag, the agitation may also be arranged by pressing or squeezing the bag appropriately from the outside. With the magnetic tool, the sample contained in the bag can also be agitated efficiently, as the bag allows for repeated movement back and forth.

The magnetic tool is used to collect the magnetic particles introduced into the sample contained in the sample container and to remove them from the sample container for various further processing operations. The magnetic tool can also be used to agitate the sample as required. The magnetic tool is a means including a magnet, a permanent magnet or electromagnet, wherein the magnet is introduced into the sample and the magnetic particles contained in the sample are collected around the magnet by means of magnetic force. The magnetic particles may also be already attached to the surface of the protective membrane. The magnet may be protected with various fixed coatings, such as e.g., epoxy polymer or teflon. The magnet may also be protected by a protective membrane made of an elastomeric, stretchable material. The magnet protection may also be made of a non-elastomeric material, such as polypropylene. A metallic magnet protection is also possible.

The magnetic tool may simply be a means with a handle, a mechanism for moving the permanent magnet, a locking mechanism for positioning the permanent magnet and a changeable protective tip of the magnet. The magnetic tool may have various shapes and sizes. The magnet may be rod-like, a ball, plate-like or of an indefinite shape according to different needs. The magnet may be constituted of several permanent magnets and combinations of ferromagnetic material. The magnet may incorporate magnets that are magnetised in different directions or magnets that include several different magnetic field solutions.

One of the essential technical characteristics of the magnetic tool according to the invention is that the magnet field strength and alignment can be adjusted in relation to the protective membrane surrounding the magnet. This can be achieved by moving the magnet in a ferromagnetic tube so that the magnet can be entirely inside the tube, in which case the power of the magnet is minor or zero, or the magnet may be partially or entirely outside the tube, in which case the power and the collecting surface of the magnet are in proportion to the protruding portion of the magnet. The tube may be made of iron or another suitable material having magnetic properties suitable for preventing the magnetic flow from passing through the tube. The power of the magnet can be adjusted by changing the position of the magnet in relation to the ferromagnetic tube so that part of the magnet is inside the tube. Alternatively, the magnet may be kept in place and the ferromagnetic tube moved in relation to the magnet. The magnet has been fastened to a rod, which may be ferromagnetic or is not ferromagnetic, and which makes it possible to move the magnet inside the ferromagnetic tube.

The protective membrane of the magnet may be suitably shaped to protect magnets of different sizes and shapes. The protective membrane may also have special areas for collecting magnetic particles in a desired manner, for example right into the lower portion of the protective membrane. The fastening of the protective membrane of the magnet may be realised by matching the protective membrane and the magnetic tool to one another in such a suitable way that the protection can be pressed/pushed into contact with the magnetic tool. The protective membrane of the magnet may also be fastened to the tool with the help of a special locking mechanism. The protective membrane of the magnet may also be designed in such a way that the same protection can be used to protect several separate magnets. When the protective membrane of the magnet is made of an elastomeric material, the protection used in the starting situation may even be a flat elastomeric membrane that is stretched, with the help of the magnetic tool, around the magnet to form a suitable protective membrane. The protective membrane of the magnet may also be a pre-shaped elastomeric protection that can be stretched by means of the magnet suitably, as required, to form a thinner membrane around the magnet. The magnetic tool may have different bushing/tube systems, which make it possible to stretch the elastomeric protection, keep it stretched or reduce stretching. A ferromagnetic bushing may also serve this purpose.

The protective membrane may be of an unstretchable material, such as e.g. polypropylene, polystyrene, polycarbonate, polysulphone and polyethylene. The protective membrane may also be of a non-ferromagnetic metal or ferromagnetic metal. The protective membrane may also be of a stretchable elastomeric material, such as e.g. silicone rubber, fluoroelastomer, polychloropropene, polyurethane or chlorosulphonated polyethylene. The protective membrane may also be treated with special substances to change the properties of the protective membrane. The protective membrane may thus be coated with e.g. teflon (PTFE, Polytetrafluoroethylene). It is particularly important to be able to choose the protective material and any further treatment so that the end result enables the apparatus to function according to the invention even when used with very strong or corroding chemicals. The protective membrane may also be shaped so that it enables the protection of several separate magnetic units, e.g. in apparatuses with 8, 12 or 96 channels. The protective membrane may be tubular, sheet-like or irregularly shaped. There are particularly numerous options when using an elastomeric protective membrane, as in this case the magnet encased and the ferromagnetic tube can also shape the protective membrane.

One preferred alternative for the protective membrane is a flat or plate-like protective membrane of a stretchable material. Such a protective membrane may be a single, stretchable membrane placed in a special frame. The purpose of the frame is to facilitate the use of the protective membrane and to provide the membrane with properties suitable for stretching. Another alternative is a roll-type embodiment, whereby the protective membrane may be changed by simply unwinding new membrane from the roll. This alternative may also include the use of a frame, a special support or bracket while the protective membrane is being stretched during actual use. The use of such a protective membrane comprised of one sheet is a highly recommended alternative when the aim is to reduce material consumption during isolation and purification operations. The use of a sheet-like protective membrane is also less expensive than the use of shaped and large-sized protective membranes manufactured with mould tools.

With the magnetic tool, the magnetic particles can be collected from a large sample volume and transferred into an essentially smaller volume or directly onto a culture plate, for example. To concentrate the magnetic particles to a very small volume, it is necessary to use a special concentration unit. The concentration unit is designed so that the protective membrane of the magnetic tool and the containers used for the concentration are highly compatible with each other, which allows the solution contained in the container to be made to rise to the desired level by placing the protective membrane at the bottom of the container. The container and the protective membrane may have suitable guiding apparatuses or guides for centering the protection in relation to the container. It is not recommendable to allow the protective membrane to come into contact with the inner walls of the container and the particles to come loose from the surface of the protective membrane. The centering of the protective membrane may also be arranged with bulges/recesses arranged on the inner walls of the container or on the outer walls of the protective membrane. In this case, the protection is allowed to come into contact with the walls of the container in a controlled manner, so as to provide centering.

In the enrichment unit according to the invention, the sample container may include compartments for one or several samples, and the compartments may be isolated from one another by means of special protrusions/recessions.

The magnetic tool may have one or several magnets, and ferromagnetic material may be arranged in connection with the magnets. The magnetising direction of the magnets may vary, and the various magnets included in the same magnetic tool may have magnets that are magnetised in different directions. The magnet may be a large-sized, powerful permanent magnet, which is located inside the protective membrane. The permanent magnet can be moved to provide a magnetic field at the desired location outside the protective membrane and also to eliminate the magnetic field. With a ferromagnetic bushing, the magnetic field of the magnet located inside the protective membrane can also be controlled. When the magnet is located inside the ferromagnetic bushing, the magnet has no magnetic field of a significant magnitude outside the ferromagnet. The magnetic field outside the protective membrane can be controlled by moving the magnet and the ferromagnetic bushing suitably in relation to each other. The magnet may also be an electromagnet or a ferromagnetic object with a magnetic field induced from the outside.

According to one preferred embodiment, the magnetic tool does not have a detachable protective membrane, but the magnet is provided with a suitable protective coating. Such a coating protects the magnet against corrosion and resists various washing and decontamination treatments. The purpose of all magnetic tools is to efficiently collect a biological component from a large sample volume on the surface of the protective membrane, to transfer the biological component on the surface of the protective membrane away from the sample and to concentrate the biological component to a smaller volume.

Particularly efficient concentration is achieved with an enrichment unit according to one embodiment of the invention, in which enrichment unit the protective membrane of the magnetic tool and the concentration container have very good compatibility. In such a case, the amount of solution contained in the concentration container does not have to be large to cause the solution level to rise above the particles located on the surface of the protective membrane. When the protective membrane is introduced into the solution, the protective membrane replaces the solution and the replaced solution rises upward in the space between the protective membrane and the concentration container. The solution level can be raised to the desired height by suitably optimising the shapes of the concentration container and the protective membrane and the amount of solution used in the container. The particles can now be released from the surface of the protective membrane by eliminating the magnetic field around the protective membrane. The release of the particles into the solution can be accelerated and enhanced by moving the protective membrane in the solution. After this, the protective membrane is removed from the solution, and the solution returns to its original place at the bottom of the concentration container. The particles can be homogenised in the solution, if required. To concentrate the particles even more, the particles contained in the solution can be collected using a small magnet and transferred into another container containing an even smaller amount of solution.

A preferably small magnet is located in the very end portion of the protective membrane of the magnetic tool, in which case it is physically possible to bring the particles to a small volume. To transfer the particles into the solution contained in a very small container, a very small and slender protective membrane can be used. For this purpose, another protective membrane and a different magnetic tool can be used. This situation can also be achieved using the same magnetic tool and the same protective membrane that was used for catching particles from a large volume. In this case, the lower portion of the protective membrane is shaped to be suitably slender to make it possible to introduce the particles into a small container, such as a PCR tube, a well in a 96 microplate or 384-plate. A particularly suitable solution for realising such an application is offered by a so called hybrid magnetic tool having a relatively long protective membrane and at least two magnets inside the same protective membrane. The first magnet is of a large size and its purpose is to collect particles efficiently from a large volume on the surface of the protective membrane. The magnetising direction of this magnet is preferably perpendicular to the longitudinal axis of the protective membrane, in which case the magnet collects particles on a large area on the surface of the protective membrane. This magnet is located in the middle or upper portion of the magnetic tool. The second magnet is small and located in the lower portion of the magnetic tool right at the very end of the protective membrane. The magnet may be of a different shape, depending on the shaping at the end of the protective membrane. The magnetising direction of this magnet may vary, but its purpose is to collect particles into the very end portion of the protective membrane. When the particles are collected into the very end portion of the protective membrane, further concentration stages can be performed efficiently.

The end of the protective membrane may be suitably shaped so that it fits inside very small containers. The end portion of the protective membrane may be particularly long and slender and have different shapings. The end of the protective membrane may have a round, sharp, conical or flat shape as required. If the protective membrane is made of a non-elastomeric material, the above-mentioned shapings are already incorporated in the protective membrane. When elastomeric material is used for the protective membrane, the end shaping can be influenced, for example, by magnets located inside the protective membrane and by other structures. The magnet may be used to stretch the protective membrane from the inside, and as the protective membrane stretches, it also adapts itself to the shape of the magnet. A protective membrane made of elastomer may have a suitable pre-shaping, and stretching may be applied to achieve additional shaping as required. The magnetic tools and protective membranes described here may be manual or they may be part of an automated set of apparatuses. The magnet solutions may be individual ones, if samples are to be handled one at a time. The magnet solutions may also be multiples of 8, 12, 24, 28 or 96, for example, if several samples are to be handled simultaneously. The protective membranes may also be individual or they may include places for several magnetic tools.

One type of solid phase used in the enrichment method according to the invention consists of a non-particulate structure coated with a specific affinity ligand. The solid phase according to the invention is, for example, a magnet, which is fastened e.g. to a ferromagnetic rod or another structure. The structure to which the magnet is fastened is, for example, a stiff, flexible wire-like structure or another similar support structure. The structure to which the magnet is fastened may also be a magnet. A rod-like stick, for example, coated with e.g. an antibody or a particle, is a solid phase according to the invention.

One preferred embodiment is a magnet located inside the protective membrane, with magnetic particles over a large area on the protective membrane collecting the desired biological component from the sample. The particles have been collected with the magnet on the surface of the protective membrane before the protective membrane is introduced into the sample. With the particles already fastened, the possibility of the particles remaining in the sample is almost completely eliminated. Such rod and wire structures can, according to the invention, be handled with the help of the lead-through structure described in the invention.

A particularly practical and efficient embodiment of the enrichment unit according to the invention is provided by a set of apparatuses wherein the lead-through structure works together with a sample container having several compartments for the samples. The samples can be dosed into the compartments through the openings provided in the lead-through structure. The particles for collecting one or several biological components from the sample can also be introduced through the same openings. The lead-through structure suitably isolates separate samples from one another while preventing cross-contaminations between samples. The samples can safely be agitated in a laboratory shaker, for example, with the lead-through structure serving as a kind of plug on top of the sample container. The magnetic tools can be placed on the lead-through structure and the collection of the particles from the sample is effected by holding the magnet of the magnetic tool in the position for collection. As the magnetic tools are introduced into the sample through the openings provided in the lead-through structure, the magnetic tools may also be left on top of the lead-through structure to collect particles from the sample. The lead-through elements may be developed so that they hold the magnetic tools securely in place, even if the sample container is simultaneously agitated in a shaker. The agitation improves and accelerates the collection of particles on the surface of the magnetic tool's protective membrane. Once the particles have been collected from the sample with the help of the magnetic tool, the particles can be washed, concentrated and/or taken for appropriate determination.

The object of the invention is also a biological component enrichment method for the isolation, purification and/or determination of a biological component using particles and/or another solid phase. The purpose of the invention is also to provide an enrichment method which does not involve the above-mentioned problems.

The biological component enrichment method refers to a method suitable for the growing, isolation, purification, enrichment and determination of bacteria, viruses, proteins and nucleic acids.

Method According to the Invention

When processing larger volume samples, the easy and efficient handling of the sample material presents a great challenge. When a small amount of biological components is to be captured from a large volume, it must be possible to bind the desired components efficiently to the solid phase, such as on the surface of the particles, to isolate the particles from the rest of the sample and finally, by washing, to concentrate the particles and the isolated component to the desired solution. The biological components may, for example, be bacteria, yeasts, moulds, viruses, parasites, cells, cell organelles, proteins, peptides, toxins, nucleic acids, hormones, polysaccharides, allergens or various haptens.

Characteristics of the Method According to the Invention

The biological component enrichment method according to the invention can be used to isolate and concentrate a limited number of biological components from a large sample volume. The enrichment method according to the invention can also be used to grow cells. In one of the applications of the method according to the invention, bacteria are grown, isolated, washed, concentrated and introduced onto a culture plate and/or taken for other determination methods, such as various nucleic acid amplification methods (e.g. NASBA, Real-Time PCR and LCR). One of the essential characteristics of the enrichment method according to the invention is its broad field of application.

When using the enrichment method according to the invention for growing bacteria or cells, for example, the agitation of the solution in the sample container may be arranged in many different ways, if required. The sample container and the lead-through structure may be placed on top of a special laboratory shaker. If the sample container is of a resilient material, the sample container can be efficiently agitated by squeezing the sample container in a suitable manner. A special agitator can be introduced into the sample through the lead-through structure, or the stick/solid phase/magnetic tool introduced through the lead-through structure may be used for agitation. Especially when the sample container is of a resilient material, such as e.g. a stomacher bag, the sample can be agitated with a magnetic tool or another stick-type structure while the magnetic tool is fastened to the bag.

In the method according to the invention, the heating of the sample container can be arranged by placing the sample container in incubators that are commonly used in laboratories or on a water bath. Aeration can be arranged, for example, by bubbling the sample through a hose using a compressor.

By using the method according to the invention, the desired biological component can be collected from a large volume to a significantly smaller volume and, when needed, the concentration of the component in the sample can be determined.

By using different solid phases, the method according to the invention can be applied in several different areas. The solid phase may consist of particles of different sizes and particles of different sizes may be contained in the same sample. The particle may be round, rod-like or an object of an indefinite shape. The particle may be a magnet, or of a magnetisable and/or non-magnetisable material. The particle may also have a special area containing ferromagnetic or magnetic material. The function of the said material is to make it possible to handle the particle with the magnets, as the particle would otherwise remain stationary in the magnetic field. The diameter of the particles is usually within the range of 50 nm to 5 cm. Some of the particles placed in the sample may collect the desired biological component, while others may have the task of collecting other particles around them or of forming aggregates with other particles. A specific affinity ligand, such as e.g. an antibody, can be labelled with biotin, for example. Such a labelled or non-labelled antibody may be freely present in the sample and bind specifically to the biological component. The solid phase present in the sample may be coated in such a way that it binds either directly to the biological component or to the affinity ligand bound to the biological component.

Different alternatives are preferred in situations, where, for example, such particles are to be used that do not sediment quickly and are not magnetisable or are very poorly magnetisable. In order to use a magnetic field to facilitate the handling of the solid phase, larger particles or particles containing more magnetite may be added. With the help of these particles, which can be more efficiently controlled and moved by means of a magnetic field, it is possible to use magnets for handling the above-mentioned non-magnetisable particles.

The particles used in the enrichment method according to the invention may incorporate affinity ligands, enzymes, antibodies, bacteria, cells or cell organelles. The binding of the desired components may also be achieved by selecting the surface properties of the used microparticles and the composition of the buffers appropriately so that they are suitable for binding the desired components from the samples. Examples include ion exchange-, hydrophobic and reverse phase chromatography. In these cases, the binding and release of the proteins from the surface of the microparticles, for example, is performed with suitably selected buffers and solutions. Salt concentration and pH, for example, are in this case very important factors.

The affinity ligand may be, for example, a single- or two-stranded nucleotide sequence, such as DNA (Deoxyribonucleic Acid), RNA, mRNA or cDNA (Complementary DNA), or PNA (Peptide Nucleic Acid), protein, peptide, polysaccharide, oligosaccharide, a small-molecular compound or lectin. The affinity ligand may also be one of the following: Ovomucoid, ProteinA, Aminophenyl boronic acid, Procion red, Phosphoryl ethanolamine, Protein G, Phenyl alanine, Proteamine, Pepstatin, Dextran sulfate, EDTA (Ethylenediaminetetraacetic Acid), PEG (Polyethylene Glycol), N-acetyl-glucosamine, Gelatin, Glutathione, Heparin, Iminodiacetic acid, NTA (Nitrilotriacetic Acid), Lentil lectin, Lysine, NAD (Nicotinamide Adenine Dinucleotide), Aminobenzamidine, Acriflavine, AMP, Aprotinin, Avidin, Streptavidin, Bovine serum albumin (BSA), Biotin, Concanavalin A (ConA) and Cibacron Blue.

The immobilisation of the affinity ligand to the particles may also mean that the ligand is fastened to the surface of the particles or that it has been captured inside a "cage-like" particle so that the surrounding solution may come into contact with it. The fastening of the affinity ligand to the particles may be performed by means of covalent binding, for example with amino or hydroxy groups contained in the phase. Alternatively, binding may be achieved by means of a bio-affinity pair, e.g. a biotin/streptavidin pair. According to one method, the enzyme to be immobilised is produced using recombinant DNA technology, for example in *Escherichia coli* bacteria, and the enzyme has been provided with a specific affinity tail. This affinity tail binds to the microparticles, which have a suitably fastened component that binds strongly to the said affinity tail. The affinity tail may be a small-molecular compound or protein.

Various magnetic tools may be used in the method according to the invention to isolate the particles contained in a large sample volume from the sample container and to efficiently concentrate the particles to a smaller solution volume.

In one enrichment method according to the invention, the particles are taken, on the surface of the protective membrane, directly onto the culture plate. The particles may be distributed over one or several plates. Using a long permanent magnet magnetised in a direction perpendicular to its longitudinal axis, the particles can be distributed conveniently over two different culture plates. On the culture plate, the particles may be spread to cover the entire surface of the culture plate, using the same protective membrane for spreading the particles. This eliminates the need to use sterile spreading rods to spread the particles.

The use of an elastomeric protective membrane is a particularly gentle and reliable way to spread the particles on the culture plate surface without damaging the agar surface. Elastomeric silicone rubber is also a particularly good material for microbiological work, as silicone rubber withstands high temperatures, for example autoclaving (+120° C.).

Immunoassays may also be performed directly from the biological component collected on the surface of the particles, in which case the particle serves as the solid phase for the immunoassay. In such a case, the components bound to the particles are incubated with the anti-component antibody, which may be suitably labelled. The anti-component antibody and particle-component complex thus created is washed to remove the non-bound anti-component antibody. By adding suitably labelled anti-anti-component antibody or antimark antibody, the assay may be continued with different chromogenic, fluorescence or luminescence assays. On the other hand, the biological component may be detached/extracted from the particle surface and the assay may be continued using, for example, antibodies bound to the well of a microtiter plate as the solid phase for the immunoassay.

Nephelometric assay methods are also suitable for use in the method according to the invention. If the biological component isolated, washed and concentrated by means of particles contains nucleic acid (DNA, RNA, mRNA, plasmid DNA), the particles may either be taken directly to the amplification reaction, or the nucleic acid may be isolated and purified prior to taking them to the amplification reaction. Collecting pathogenic viruses, bacteria or parasites, for example, by means of an antibody from the sample on the surface of the particles, and taking the particles directly to the assay is an important application of the method described in the invention. The particles may be selected so that they do not inhibit the enzymes used in nucleic acid amplification reactions (e.g. PCR, RT-PCR, Real-time PCR, Strand displacement amplification, LCR and Multiplex PCR). DNA-DNA hybridisation, rolling circle amplification, Q-beta replicase, DNA fingerprint, restriction fragment-based genotyping and AFLP methods may also be used in the detection according to the method described in the invention.

The enrichment method according to the invention is particularly viable when combined with highly sensitive determination methods, such as nucleic acid amplification methods. Using the enrichment method according to the invention, a limited number of biological components can be enriched from a large sample volume and the components can be concentrated to a small volume with high purity. The impurities and inhibitors coming from the sample prevent or hinder PCR reactions, for example. The PCR method is highly sensitive, but to take advantage of the sensitivity of a method a good sample quality is required. Sample quality means the presence and purity of the sample/component to be amplified. Several commercial PCR methods are available, but methods suitable for the pre-processing and concentration of the sample have not been developed to a similar performance level. The enrichment method according to the invention allows considerably more efficient and reliable utilisation of the existing nucleic acid amplification methods than the one used at present.

Particles are generally used as solid phases in biological purification processes to bind different biomolecules, cell organelles, bacteria or cells. Particles and, particularly, purification methods based on the use of magnetic particles make it possible to handle biological samples, which are in many cases complex, without the need for centrifuging the samples. Magnetism is not a general characteristic of a biological material, which makes the use of magnetic particles an excellent purification technology for these materials.

There is an enormously wide spectrum of purification processes, as the particles may be coated with molecules or compounds that have a large variety of binding properties. The use of magnetic particles in biological processes is continuously increasing due to the ease and rapidity of isolation.

The particles according to the invention may be magnetisable particles, magnetic particles or non-magnetisable particles. The particles according to the invention may be objects with diameters ranging from a few nanometers to several centimeters. Magnetic particle usually refers to a material including a core comprised of paramagnetic or superparamagnetic material and of a polymer surrounding the core. The outer surface of the polymer may be provided with a coating capable of forming a complex with the material concerned (to be purified or isolated). The polymer may consist, for example, of polystyrene, cellulose, agarose or silica. Paramagnetic or superparamagnetic particles do not have a magnetic field, but they form a magnetic dipole in the presence of an external magnetic field.

In this context, magnetic particle also refers to particles containing ferromagnetic material. The magnetic particles may be of different sizes and preferably they have a diameter of between 0.5 and 100 μm. The magnetic particles may also be a combination of non-magnetic particles and magnetic particles. The magnetic particles may be moved by means of magnetism. The size of the microparticles used in biological processes usually ranges from 0.01 to 100 μm, in most cases from 0.05 to 50 μm. Known non-magnetisable microparticles are, for example, the solid phases used in chromatographic purifications, such as particles made of agarose and the latex particles used in quick tests based on agglutination.

For example, the microbes or cells bound to the surface of antibody-coated particles may be directly transferred, on the protective membrane/coating, to the growth medium, where the spreading preferably occurs in the method according to the invention by moving the protective membrane along the agar surface of the growth medium. The particles and the microbes or cells bound to them are detached from the protective membrane by mechanically rubbing and stroking the protective membrane along the agar surface of the growth medium. Mechanical rubbing is an efficient and reliable way of transferring all the particles collected on the surface of the protective membrane onto the culture plate.

The enrichment method according to the invention and the apparatuses belonging to the enrichment unit according to the invention, such as the magnetic tool, protective membrane, lead-through structure and the containers used allow for the large-volume sample containing a biological component to be concentrated very efficiently. By using the enrichment method and enrichment unit according to the invention a solution is achieved that is optimal to be used widely for collecting a biological component, by means of particles, from a large sample volume, for washing impurities off the particle pellet and for concentrating the biological component to a small volume/on the surface, for example for the purpose of determination. The enrichment method and enrichment unit according to the invention are particularly helpful when enriching a limited number of biological components from a large volume to a small volume.

The enrichment unit and enrichment method according to the invention can be used for processing large sample volumes and when the aim is to concentrate a biological component to a small volume or, for example, onto the agar surface of a culture plate.

The enrichment method and enrichment unit according to the invention allow for the following solutions and properties:
1. Growing of cells and bacteria.
2. Enrichment of a biological component from a large amount of liquid.
3. Processing of a large amount of biological component.
4. The compatibility of the lead-through structure with different sample containers.
5. The functioning of the lead-through structure with the sample container for growing bacteria/cells, preventing sample cross contaminations, reducing sample evaporation, as a dosing channel for solutions/particles, providing a space for the incubation of particles and providing a stand for the magnetic tool during particle collection.
6. Providing support for and using bags and containers that do not keep their shape by themselves by means of the lead-through structure.
7. The use of the lead-through structure with a magnetic tool.
8. The use of the lead-through structure for arranging sample aeration and agitation.
9. The use of particles and magnets for collecting biological components.
10. Collecting one or several biological components from the sample simultaneously.
11. Concentration of the particles to a small volume.
12. Transfer of the particles, using the protective membrane, onto surfaces, such as the agar surface of a culture plate.
13. The handling of particles when using a rigid protective membrane.
14. The handling of particles when using a stretchable, elastomeric protective membrane.
15. The handling of particles when using a coated magnet.
16. A particle washing and concentration unit.
17. Shaping of the protective membrane end when transferring particles into very small containers.
18. Taking the biological component for determination together with the particle.
19. Pre-processing of the biological component, such as purification of nucleic acid prior to determination.
20. The determination of the biological component bound to the particles by plating, immunoassay, PCR, Real-time PCR, NASBA, LCR or other determination methods.
21. The release of particles into a small amount of liquid.
22. Efficient agitation.

Applications of the Invention

The enrichment method according to the invention is suitable for use in a wide variety of applications, such as purification and fractioning of proteins, purification of plasmid DNA, analysis of GMO samples, purification of genomic DNA, enrichment and determination of pathogenic bacteria, growing of bacteria, yeasts and cells, isolation and fractioning of cells, enrichment of viruses/phages, enrichment of parasites, isolation and purification of cell organelles, enrichment and determination of toxins and poisons, isolation and assay of allergens and hormones.

The described method can also be widely used for growing and isolating cells. Interesting cells include stem cells, B-lymphocytes, T-lymphocytes, endothelic cells, granulocytes, Langerhans' cells, leucocytes, monocytes, macrophages, myeloid cells, Natural Killer cells, reticulocytes, trophoblasts, cancer cells, transfected cells and hybridoma cells. Generally known methods, such as the direct or reverse cell isolation method, can be used for the isolation of cells. The first-mentioned direct isolation method consists of separating the desired cells from the sample by binding them to the particle surface, for example by using specific antibodies. In the indirect method, not the desired cells, but all the other cells contained in the sample are bound to the particles. In this case, the desired cells remain in the solution The method according to the invention is well suited for the growing, isolation, purification and/or enrichment of bacteria, viruses, parasites, yeasts and many other single- or multiple-cell organisms. A particularly important field of application is the enrichment of pathogenic bacteria, such as *Salmonella, Listeria, Campylobacter, E. coli* O157 and *Clostridium*, of viruses, parasites, Protozoa or other microorganisms from a large sample volume. The apparatus and method according to the invention can also be utilised in these areas of application.

The purification of nucleic acids involves greatly varying needs for purifying genomic DNA, plasmid DNA, total RNA and mRNA. The enrichment method according to this invention allows nucleic acids to be isolated efficiently from large sample volumes by utilising the lead-through structures of the sample container, agitations and mechanical rubbing of the particle pellet during the purifications.

The enrichment method according to the invention allows culture/growing, isolation and purification operations to be chained together according to different needs. It is, for example, possible to grow the desired cells in suitable conditions first and then enrich the cells after growing. After this, cell organelles, for example, can be isolated from the cells. The cell organelles can be purified and the process can be continued, for example, by DNA or protein purification. During the process, a variety of microparticles provided with different coatings and properties can be used according to needs. The final stage may consist, for example, of the concentration of the purified product to the desired volume, the amplification and detection of the product.

EMBODIMENTS

In the following, the invention is described using examples with reference to the appended drawings, in which

LIST OF FIGURES

FIG. 1 is a schematic side view of an enrichment unit according to the invention.

FIGS. 2*a*-2*j* are schematic side views showing the operating stages of the enrichment unit in FIG. 1.

FIGS. 3*a*-3*b* are schematic views showing the agitation stages of the enrichment unit.

FIGS. 5a-5f are schematic side views showing the operation of an automatic enrichment unit.

FIG. 7 is a perspective view of an automatic enrichment apparatus according to the invention.

FIGS. 8a-8j are schematic side views showing the operating stages of the particle washing and concentration unit.

FIGS. 9a-9e are schematic side views showing the uses of an elastomeric protective membrane and a ferromagnetic bushing in a magnetic tool.

FIGS. 10a-10f are schematic side views showing the uses of a non-elastomeric protective membrane and a ferromagnetic bushing in a magnetic tool.

FIGS. 11-14 are schematic views of different particle options in the enrichment method according to the invention.

FIGS. 15a-15c are schematic views showing a method of using a magnetic object in the enrichment method according to the invention.

FIGS. 16a-16c are schematic views showing another method of using a magnetic object in the enrichment method according to the invention.

DETAILED DESCRIPTION OF THE FIGURES

1 Bag, Cover, Stand, Magnetic Tool and Bushing Solution

Figure 1:
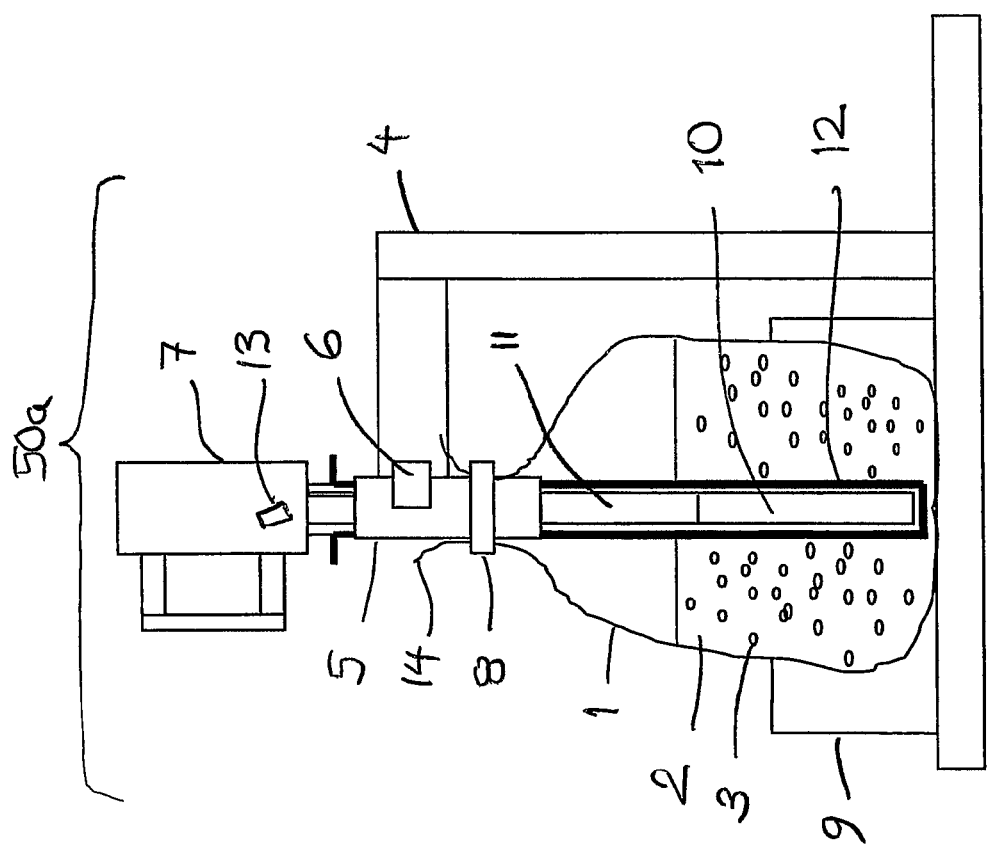

FIG. 1 shows an enrichment unit 50 according to the invention, which comprises a bag 1, a stand 4, a magnetic tool 7 and a lead-through structure 5. The bag 1, containing a sample 2 and particles 3, has been placed in a stand 4 by means of a special lead-through structure 5. The lead-through structure 5 has been fastened to the stand 4 by means of a special locking system 6. The structure formed by the lead-through structure 5 and the stand 4 serves as a bracket for the magnetic tool 7, when the magnetic tool 7 is used for collecting particles 3 from the sample 2 contained in the bag 1. The lead-through structure 5 may be formed of several separate bushing-like or tube-like structures, and the lead-through structure 5 may have several separate openings giving access to the bag. Through the lead-through structure 5, a hose or another assembly relating, for example, to aeration, can be introduced into the sample 2 contained in the bag 1, separately or simultaneously with the magnetic tool 7. Through the lead-through structure 5, various solutions or particles can also be introduced into the sample 2. The agitation of the sample 2 may also be arranged by introducing a special agitator into the sample 2 through the lead-through structure 5.

The bag 1 is fastened, by its upper portion, around the lead-through structure 5 with a sealer 8, by means of which the orifice of the bag 1 can be sealed tightly and tightened around the lead-through structure 5. If required, the bag 1 may be surrounded by special structures 9, intended to give the bag 1 additional support, keeping the bag 1 in a suitable shape, contributing to the agitation of the sample 2 contained in the bag 1 and/or facilitating the handling of the bag 1. According to one embodiment, the structure 9 has a special adhesive, which enables the fastening of the structure to the outer side of the bag. By fastening from the outside on the bag it is possible to close or open the bag orifice simply by moving the structures 9. The structures 9 may be an integral part of the stand 4 or the structures may be separate or part of another set of apparatuses, such as the agitation mechanism for bag 1. The structures 9 may also form a special trough structure, into which the bag 1 can be introduced. The trough structure may, for example, contain water or the trough structure may be part of a water bath for heating/cooling the bag 1.

The magnetic tool 7 may have a differently magnetised permanent magnet 10, fastened to a rod 11. There may be several permanent magnets 10 and they may be attached to each other by magnetic force or there may be ferromagnetic material or non-ferromagnetic material between the magnets. The magnet 10 may also be an electromagnet. The magnet 10 is surrounded by a protective membrane 12, which may be made of an elastomeric material or a non-elastomeric material. The magnetic tool 7 may incorporate mechanisms 13 for moving, for example, the permanent magnet 10, other structures, such as ferromagnetic bushings, for switching the electromagnet 10 on/off or detaching the protective membrane 12 from around the magnet 10. The magnetic tool 7 may also have special shapings that facilitate the use of the magnetic tool 7, such as an ergonomic handle structure for the hand. The stand 4 may be placed in an incubator and/or the stand 7 may be contained in an agitator, in which case the sample 2 contained in the bag 1 can be suitably heated and agitated as required. The bag 1 in FIG. 1 may, for example, be a stomacher bag intended for the homogenisation of food samples. The bag 1 may be of different shapes and made of different plastic materials, for example.

2 Collecting and Moving Magnetic Particles from the Bag

The series of illustrations in FIGS. 2a-2j shows the collection and transfer of magnetic particles 3 from the bag 1. In the series of illustrations 2a-2j, the isolation and enrichment of the particles 3 are effected with the help of the magnetic tool 7 from the sample 2 contained in the bag 1 using the means according to the invention. In FIG. 2a, the bag 1 is placed on the stand 4. The bag 1 contains the sample 2 and the particles 3. In FIG. 2b, the bushing 5 is introduced into the stand 4 and the bushing is locked into the locking system 6 incorporated in the stand. In FIG. 2c, the orifice 14 of the bag 1 is pressed around the bushing 5. In FIG. 2d, the orifice 14 of the bag 1 is closed tightly around the bushing 5 by means of the sealer 8. In FIG. 2e, the magnetic tool 7 is inserted through the bushing 5 into the sample 2 contained in the bag 1. The magnet 10 in the magnetic tool 7 is in its lower position and the magnetic field is focussed on the particles 3 around the protective membrane 12 of the magnet 10. The magnetic tool 7 may be left to rest in its place in the bushing 5 fastened to the stand 4 for the desired length of time. In FIG. 2f, the magnetic tool 7 collects, by the magnetic force of the magnet 10, particles 3 from the sample 2 around the protective membrane 12 of the magnet 10.

In FIG. 2g, the magnetic tool 7 is lifted up through the bushing 5 in the stand 4. The particles 3 that were contained in the sample 2 in the bag 1 have been collected into a pellet around the protective membrane 12 of the magnet 10, and the sample 2 no longer contains any particles. In FIG. 2h, the particles 3 collected with the magnetic tool 7 have been introduced into the solution 16 contained in the tube 15. The level of the liquid 17 in the tube 15 has risen, due to the introduction of the end of the magnetic tool 7, to a level 16, the magnet 10 being below the liquid level 16. In FIG. 2i, the magnet 10 in the magnetic tool 7 has been moved into its upper position and the magnetic force has been removed from the space containing the particles 3 around the protective membrane 12. According to one embodiment, the rod 11 in the magnetic tool may have moved into its upper position in a direction parallel to the magnet 10. The level 16 of the solution 17 in the tube 15 has been suitably arranged to remain below the magnet 10. By moving the magnetic tool 7 in the solution 15, the particles 3 are homogenised away from the surface of the protective membrane 12 into the solution 17. FIG. 2j shows a situation where the magnetic tool 7 has been taken out of the tube 15 and the surface of the solution 17 has sunk to its normal level. The particles 3 have been transferred away from the bag 1 and concentrated to the small solution volume 17 in the tube 15.

3 Sample Agitation in the Bag

FIGS. 3a and 3b show the agitation of the sample 2 in the bag 1. FIG. 3a is a front view of the stand 4 and the bag 1 is in the stand 4, tightened around the lead-through structure 5 by means of the sealer 8. The magnetic tool 7 is placed in the bushing 5 and the magnet 10 of the magnetic tool 7 is in the sample 2. The bag 1 is surrounded by structures 9a and 9b, which move to the left while the stand 4 remains stationary. The structure 9a pushes the left side of the bag inwards and the structure 9b yields, i.e., moves to the right. In FIG. 3b, the directions of movement of the structures 9a and 9b are reversed in relation to those shown in FIG. 3a. By repeating the movements of the structures 9a and 9b shown in FIGS. 3a and 3b, the sample 2 and the particles 3 in the bag 1 can be efficiently agitated. The structures 9a and 9b may also have opposite movements, i.e. the structures 9 in a way pump the bag walls from both sides in- and outwards simultaneously. In this case, the level of the liquid 2 in the bag 1 can be varied to a considerable extent. The optimal agitation method for each sample can be found by varying different agitation methods and speeds. The agitation method shown can also be used when the system does not include the magnetic tool 7, i.e. for example when growing bacteria and when incubating the particles and the sample. When the magnetic tool 7 is included, the agitation method shown speeds up and enhances the collection of particles from the sample around the magnet 10.

4 Entity Formed of Several Collecting Units

Figure 4:
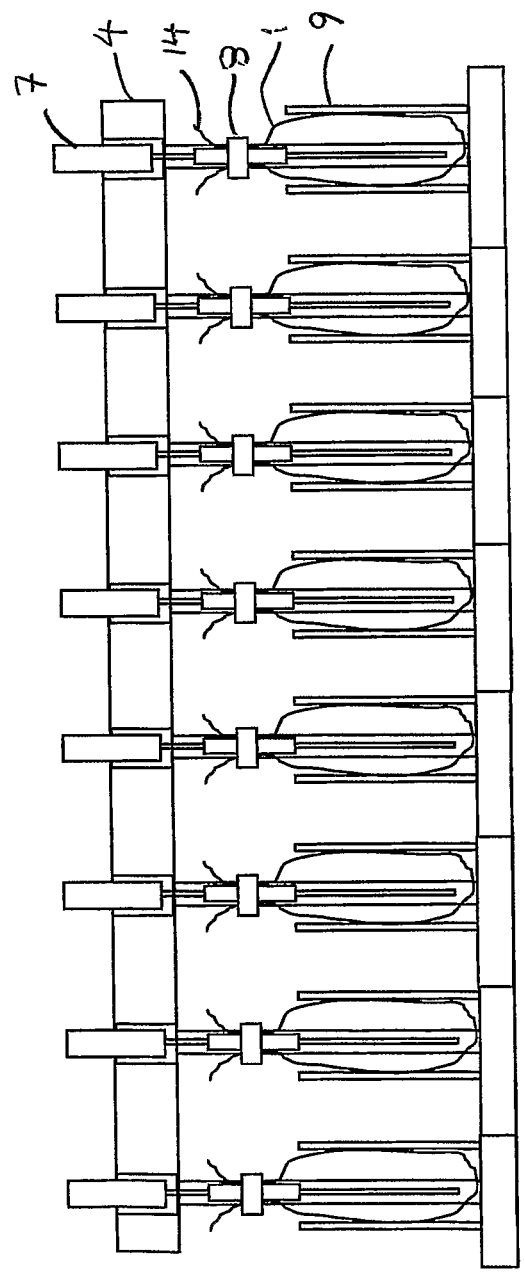
FIG. 4 is a side view of the entity formed of several collecting units.

FIG. 4 shows an entity formed of several collecting units, which entity incorporates a unit formed by several bags 1 and magnetic tools 7. The bags 1 have been fastened to the stand 4 common to all the bags 1. The structures 9 may support the bags 1 and/or agitate the bags 1. When the agitation of the bags 1 is handled by the structures 9, all the structures 9 may share the same motor. The unit shown in FIG. 4 may be placed in an incubator and/or on a shaker. The unit shown in FIG. 4 may be part of an entity incorporating heating elements, an agitation arrangement, and the entity may serve as an independent set of apparatuses.

5 Example of an Automatic Apparatus

Figure 5B:
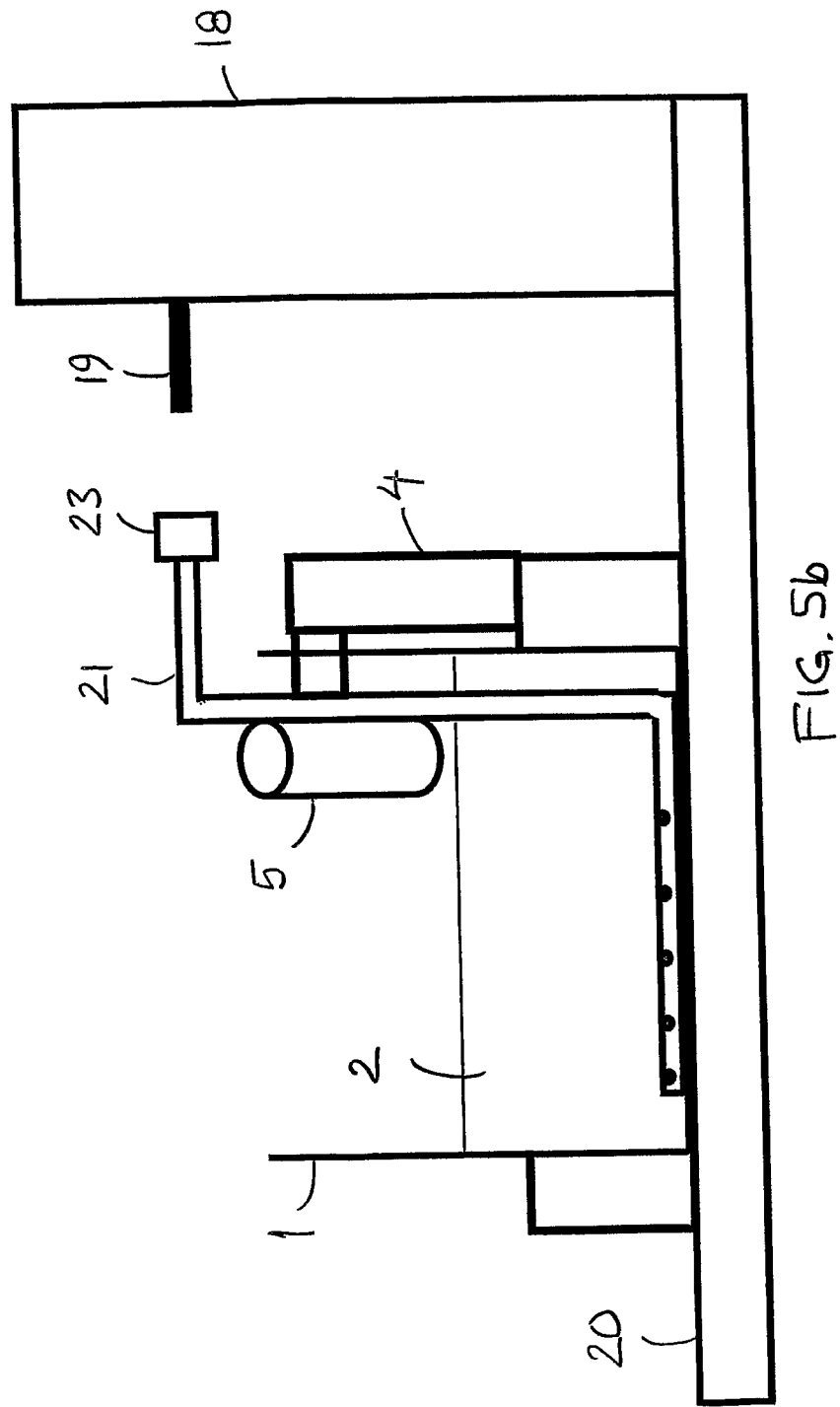

The series of illustrations in FIGS. 5a-5f show schematically the operation of an automatic apparatus 18. FIG. 5a shows an automatic apparatus 18 with a connector 19 and a worktop 20, which apparatus is meant for growing bacteria, yeasts or cells. The apparatus 18 may also be used for the purification of different biological components (e.g. viruses, bacteria, cells, nucleic acids and proteins) from different samples. The same apparatus may also be used for handling particles that are magnetic or differently magnetisable. The purpose of the particles is to collect on their surface, from the large volume sample 2 in the bag 1, biological components, such as bacteria, and to transfer the bacteria, bound to the particles, away from the bag 1. The open bag 1, in which the sample 2 has been placed in the stand 4, with the structure 9 supporting the bag 1 and keeping it in an upright position. The stand 4 and the structure 9 are on the worktop 20 of the apparatus. The stand 4 may be a detachable or an integral part of the apparatus 18.

Figure 5D:
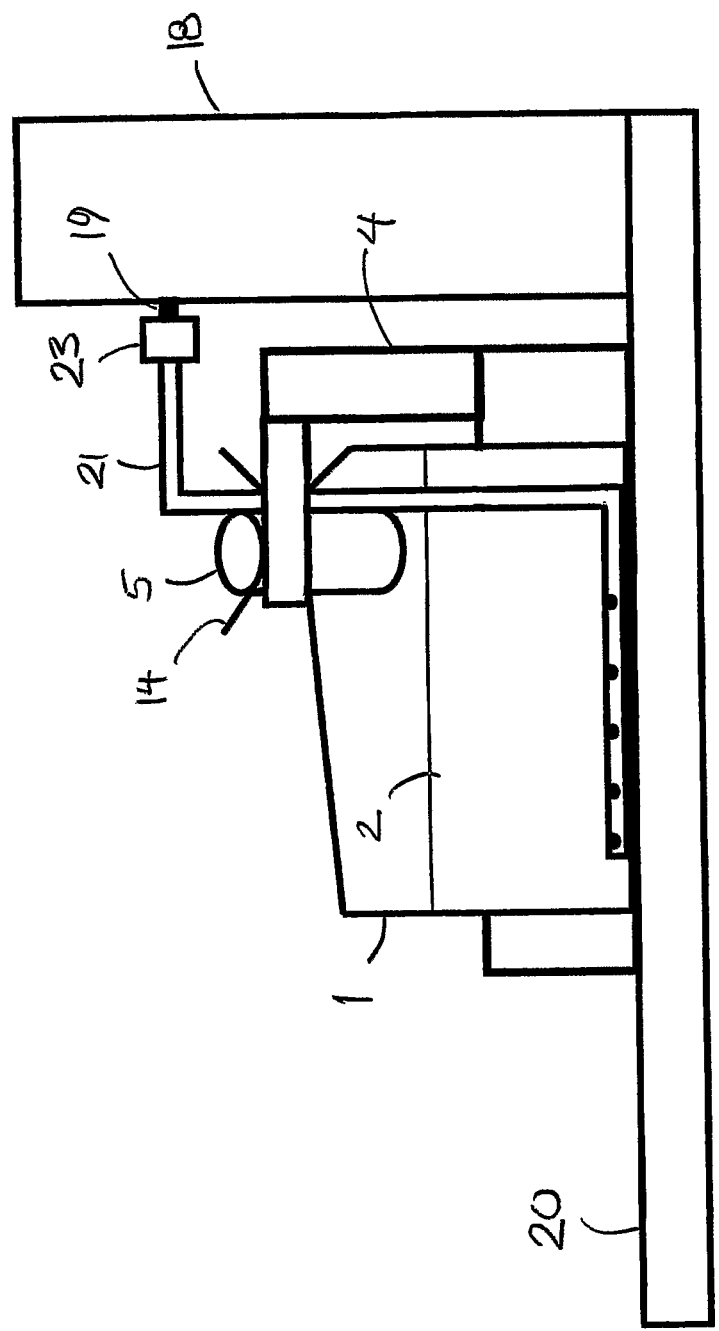

In FIG. 5b, the bag 1 contains a bushing-aeration unit 21, which has been fastened to the stand 4. The bushing-aeration unit 21 may be a single object or it may be constructed of several pieces. The bushing-aeration unit 21 includes a special lead-through structure 5 and an aeration unit with a counter-connector 23 and bubbling holes 22 in its lower portion. If no aeration is needed, the bushing-aeration unit 21 may be replaced by a lead-through structure intended to insert the magnetic tool through into the bag 1 and into the fastening of the bag 1. In FIG. 5c, the orifice of the bag 1 has been closed around the bushing-aeration unit 21 by means of the sealer 8. The sealer 8 has been fastened to the stand 4, which also provides firm support for the bag 1. In FIG. 5d, the bag 1 and the bushing-aeration unit 21 have been moved, in the stand 4, on the worktop 20, towards the rear edge of the apparatus 18. The counter-connector 23 of the bushing-aeration unit 21 has been connected to the connector 19 of the apparatus 18. The purpose of the connector 19 is to introduce, for example, air or another gas into the sample 2 in the bag 1 through the bushing-aeration unit 21.

Figure 5E:
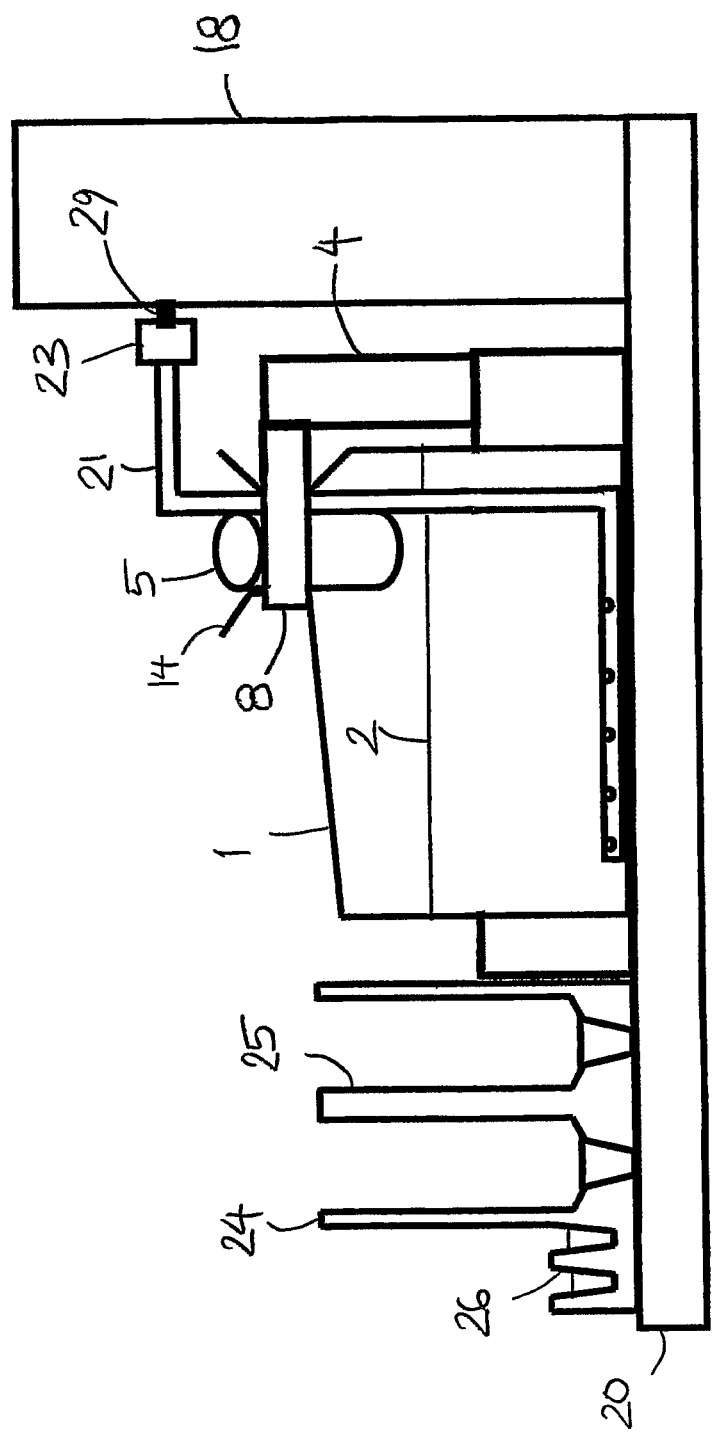

In FIG. 5e, a particle washing and concentration unit 24 has been placed on the worktop 20 of the apparatus 18. The particle washing and concentration unit 24 allows the particles to be washed and concentrated using the magnetic tool 7. The particle washing and concentration unit may have a different number of different openings 25 of various sizes containing suitable liquids, such as washing buffers. The particles may, after a suitable number of washing operations and concentration stages, be transferred into a container 26, which is the washing and concentration unit's outermost container at the front edge of the apparatus 18. From the container 26 the particles may be taken to the subsequent applications and/or determinations, such as immunoassay, nucleic acid amplification (e.g. PCR, RT-PCR, LCR and NASBA). The particle washing and concentration unit 24 may be comprised of a single piece or several separate pieces, such as tubes. According to one preferred embodiment, the particle washing and concentration unit 24 is a single integral piece, which has ready-dosed liquids and particles and wherein the container orifices have been closed for the duration of the storage.

In FIG. 5f, the magnetic tool 7 fastened with the arm 29 to the apparatus 18 has been introduced inside the bag 1 so that the magnets 10 protected by the protective membrane 12 are in the sample 2. The magnet solution of the magnetic tool 7 may incorporate various rods 28 and bushings 27. The arrows in FIG. 5f show the paths of motion allowed by the apparatus for moving the magnetic tool 7 between the bag 1 and the particle washing and concentration unit 24. The arm 29 has a track 30 along which the magnetic tool 7 can move to the left and to the right.

6 Bag Agitation

Figure 6B:
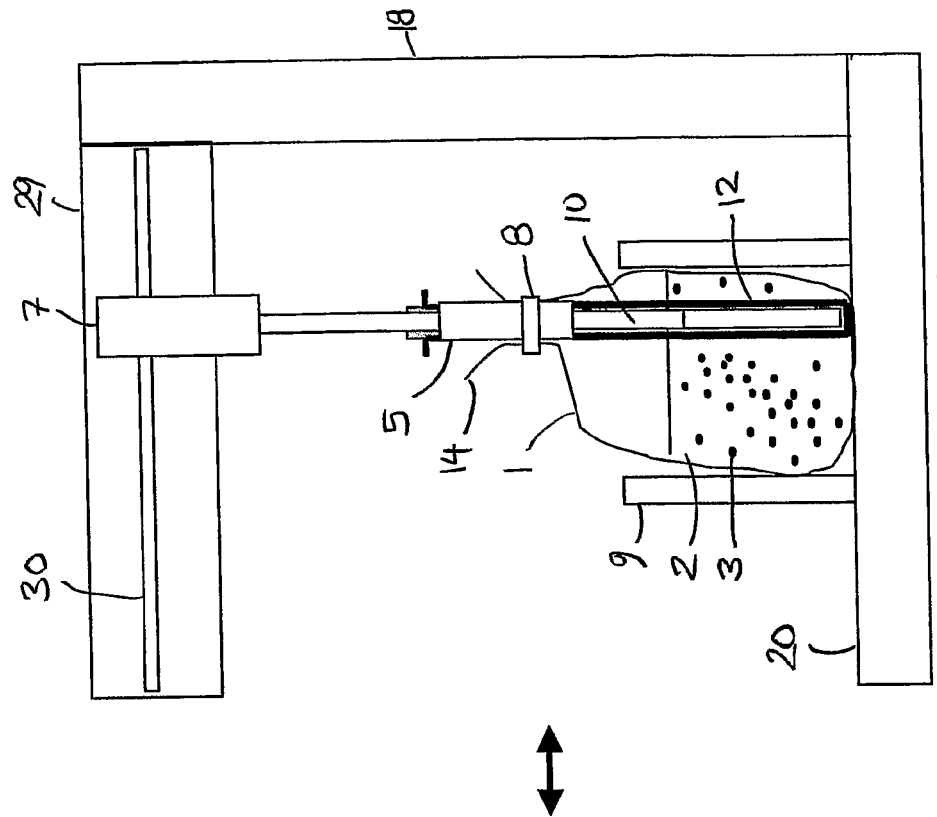
FIGS. 6a-6b are schematic side views showing the agitation of the sample in a bag with the help of a magnetic tool.
Figure 6A:
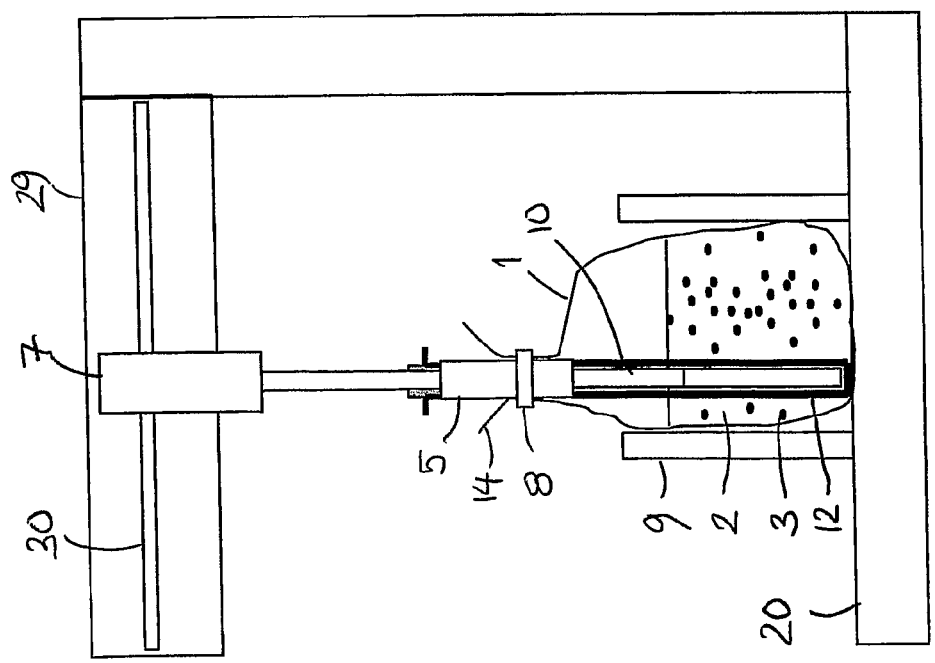

FIGS. 6a and 6b show an example of the agitation of the bag 1 in the enrichment method according to the invention. FIG. 6a shows the sample 2 agitation method when the bag 1 is made of a resilient material, such as e.g. a stomacher bag made of thin plastic for the homogenisation of food samples. In FIG. 6a, the bag 1 has been supported by the structures 9 on the worktop 20 of the apparatus 18 and the bag 1 has been fastened around the lead-through structure 5 with the sealer 8. The magnetic tool 7 is supported by the arm 23 in the apparatus 18. The arm 29 has a track 30 along which the magnetic tool 7 can move to the left and to the right. FIG. 6a shows a case where the magnetic tool 7 has been moved to the left in the bag 1 and the material of the bag flexes suitably. FIG. 6b shows a case where the magnetic tool 7 has been moved in the bag 1 to the right. By repeating the movements shown in FIGS. 6a and 6b, the sample 2 in the bag can be efficiently agitated using the magnetic tool 7. The magnetic tool 7 does not have to be used for agitation, but it can be suitably replaced by various rod structures. The magnetic tool may be used for collecting particles from the sample 2 or solely for agitating the sample 2 in the bag 1.

7 Automatic Apparatus

FIG. 7 shows an automatic enrichment apparatus 18 according to one embodiment of the invention for growing different cells and/or performing particle collection, washing and concentration. FIG. 7 shows an automatic apparatus 18 wherein several magnetic tools 7 have been fastened to the arms 29. The apparatus 18 has connectors 19 for bushing and aeration units 21. The worktop 20 of the apparatus 18 has particle washing and concentration units 24 and bags 1 placed in stand assemblies 32. The worktop 20 of the apparatus 18 is covered by a wall 44.

8 Concentration of Magnetic Particles

The series of illustrations in FIG. 8a-8j show the method for washing and concentrating the particles 3, for example, from the sample 2 in the bag 1. The bag 1 in FIG. 8a contains the magnetic tool 7 wherein the magnets 10 a and 10b are surrounded by a protective membrane 12. The magnet 10a is a permanent magnet magnetised in a direction perpendicular to its longitudinal axis, which collects particles on a large area around the protective membrane 12. The magnet 10b is smaller than the magnet 10a located at the very end of the magnetic tool 7 and is preferably magnetised so that the magnet 10b collects particles 3 into the very end portion of the protective membrane 12. FIG. 8b shows a situation where the magnetic tool 7 has been left for some time in the sample 2 to collect particles 3 around the protective membrane 12. The magnetic tool 7 may have been moved in the sample 2 to speed up the collection of particles 3 from the sample 2. The bag 1 may also have been agitated e.g. in a shaker, or the walls of the bag 1 may have been squeezed to obtain agitation in the sample 2. The magnet 10a has collected the particles on a large area around the protective membrane 12. The purpose of the large and powerful magnet 10a is to collect particles efficiently and rapidly from a large volume. The actual purpose of the small magnet 10b is to concentrate the particles 3 to a small volume.

FIG. 8c shows a situation where the magnetic tool 7 and the particles 3 collected around the protective membrane 12 have been transferred away from the sample 2 contained in the bag 1. The magnetic tool 7 is taken to the container 15, which may be part of a special particle washing and concentration unit. The container 15 contains solution 17 and the solution level 16 is low in the container 15. In FIG. 8d, the magnetic tool 7 has been taken to the bottom of the container 15, whereby the end portion of the magnetic tool 7 replaces some of the solution 17 and the level 16 rises. The shaping of the container 15 and the magnetic tool 7 in relation to one another is preferably such that they function together as a highly compatible pair. In such a case, it is possible to make even a small amount of solution move upwards a great distance in the space 31 between the container 15 and the protective membrane 12. For the successful washing and concentration of the particles 3, it is important that the level 16 of the solution 17 rises above the particles 3 collected by the magnet 10a. In FIG. 8e, the magnets 10 of the magnetic tool 7 have been transferred away from the proximity of the particles 3. The magnets need not necessarily be physically transferred away, if the magnetic field is eliminated from the proximity of the particles 3 by another means, such as a ferromagnetic bushing or electromagnet. The particles 3 can now be homogenised into the solution 17 from the surface of the protective membrane 12. The homogenisation of the particles 3 can be speeded up by moving the protective membrane in the container 15.

In FIG. 8f, the protective membrane 12 has been removed from the container 15 and the particles 3 have been re-suspended in the solution 2. In FIG. 8g, the end of the magnetic tool 7, which end contains the magnet 10b inside the end of the protective membrane 12, is introduced into the solution 2. The particles 3 are collected into the proximity of the magnet 10b around the protective membrane 12. The magnet 10a is not in the solution 2 but a considerable distance above the level 16 of the solution 2, i.e. the particles do not gather around the magnet 10a. In FIG. 8h, the magnetic tool 7 has been removed from the large container 15 into a smaller container 32. The particles 3 have gathered in the very end of the protective membrane 12 around the magnet 10b. In FIG. 8i, the magnetic field inside the protective membrane 12 has been eliminated, and the particles can be re-suspended in the solution 2 by suitably moving the protective membrane 12 in the solution 2. In FIG. 8j, the protective membrane has been removed from the solution contained in the container 32, and the particles 3 have been concentrated into the solution 2.

9 Use of an Elastomeric Protective Membrane and a Ferromagnetic Bushing in the Magnetic Tool The series of illustrations in FIGS. 91-9e shows the use of an elastomeric protective membrane and a ferromagnetic bushing in the magnetic tool and different ways of binding particles 3 to different locations on the protective membrane 12 made of elastomeric material. The series of illustrations 9a-9e shows the use of a protective membrane 12 made of elastomeric material for handling particles 3 along with the ferromagnetic bushing 27. In FIG. 9a, the magnets 10a and 10b are inside the elastomeric protective membrane 12 and inside the ferromagnetic bushing 27. When the magnets 10 are inside the ferromagnetic bushing 27, there is no significant magnetic field outside the protective membrane 12. The protective membrane 12 is fastened to the frame structure 33 of the magnetic tool 7, and the magnets are moved by means of the rod 11. The magnet 10b is fastened to the magnet 10a by means of the rod 34. In FIG. 9b, the magnet 10b has been moved out of the ferromagnetic bushing 27 and the magnet 10b is stretching the protective membrane 12. A magnetic field is focussed around the protective membrane 12 in the proximity of the magnet 10b, which magnetic field attracts particles 3 to gather around the protective membrane 12. The magnet 10b is of small size and it may be magnetised in different directions. The magnet 10a is inside the ferromagnetic bushing 27.

In FIG. 9c, the magnets 10 have been moved further and further downward, so that the magnet 10a has also come out of the ferromagnetic bushing and its magnetic field attracts particles 3. The magnet 10a is preferably magnetised in a direction perpendicular to its longitudinal axis, whereby the particles 3 gather around the protective membrane 12 all the way along the length of the magnet. The protective membrane 12 has been stretched by the magnet 10b so that it is now longer than before. FIG. 9d shows a situation where the magnets have remained stationary, but the ferromagnetic bushing 27 inside the protective membrane 12 has been moved downward around the magnet 10a. The magnetic force no longer keeps the particles 3 in contact with the surface of the protective membrane 12 in the proximity of the magnet 10a. The magnet 10b is still outside the ferromagnetic bushing 27 and can thus attract particles 3 onto the surface of the protective membrane 12. In FIG. 9e, the magnet 10b has been moved upward, so that the magnet is inside the ferromagnetic bushing 27. No significant magnetic field is exerted on the outside of the protective membrane, and the particles 3 do not therefore remain in contact with the surface of the protective membrane 12.

10 Use of a Non-Elastomeric Protective Membrane and a Ferromagnetic Bushing

FIGS. 10a-10f show the use of a non-elastomeric protective membrane 12 and a ferromagnetic bushing 27 for handling, moving and concentrating particles 3. In FIG. 10a, the particles 3 have gathered around the protective membrane 12 and in the proximity of the magnets 10a and 10b. The ferromagnetic bushing 27 is in its upper position, and the magnets 10 are outside the ferromagnetic bushing 27. The protective membrane 12 has replaced some of the solution in the container 15a and raised the liquid level 16 of the solution 2 above the particles 3 on the surface of the protective membrane 12. The container 15a and the protective membrane 12 have been shaped to be highly compatible, whereby it is possible to make the level 16 of even a small amount of solution rise high in the space 31 between the container 15a and the protective membrane 12. In FIG. 10b, the protective membrane 12 is stationary, but the ferromagnetic bushing 27 has moved downwards and the magnets 10 upwards into the ferromagnetic bushing. No magnetic forces are exerted on the outside of the protective membrane 12, and the particles 3 may be released from the surface of the protective membrane 12 into the surrounding solution 2. The protective membrane 12 may be moved suitably in the container 15a in order to release the particles 3 more efficiently.

FIG. 10c shows a situation where the protective membrane 12 has been removed completely from the container 15a and the liquid level 16 has returned to its normal level. The particles 3 have been re-suspended in the solution 2. In FIG. 10d, the protective membrane 12 has been introduced into the solution 2, which protective membrane incorporates a ferromagnetic bushing 27 containing a magnet 10a but no magnet 10b. The magnet 10b is immediately in the proximity of the end of the protective membrane 12 and attracts particles 3 to gather around the protective membrane 12. The magnet 10a is inside the ferromagnetic bushing 27 and thus incapable of attracting particles 3. This situation is favourable when the particles 3 are to be concentrated into a small area around the end of the protective membrane 12. In FIG. 10e, the protective membrane 12 and the particles 3 collected into its end have been removed from the container 15a and transferred into a smaller container 15b. Only the end portion of the protective membrane 12 is in the solution 2 and the liquid level 16 in the container 15b is above the particles 3. In FIG. 10f, the magnet 10b has been moved up into the ferromagnetic bushing 27 and the particles 3 around the protective membrane 12 have been re-suspended in the solution 2.

11-14 Different Solid Phase Alternatives

FIGS. 11-14 show different solid phase and particle alternatives for realising the method according to the invention. FIG. 11 shows small (e.g. 50 nm-100 μm) magnetic particles 3a, which can be coated with a suitable special coating, such as e.g. antibodies, phage proteins or lectins. The magnetic particles 3a collect the desired biological components from the sample on their surface. A large-sized (e.g. 1 mm-20 mm) magnet 3b is inserted into the sample, which magnet collects on its surface the smallest magnetic particles 3a contained in the sample simply by means of its magnetic force. The magnet 3b may have different shapes, e.g. a cylinder, ball or cone. The magnet 3b may be made of ferromagnetic material made into a magnet by induction. The complex 3ab thus formed may be collected from the sample using the magnetic tools according to the invention or simply a metallic rod.

FIG. 12 shows non-magnetic and non-magnetisable particles 3c, which can be coated with a suitable special coating, such as e.g. antibodies, phage proteins or lectins. The particles 3c collect the desired biological components from the sample on their surface. Magnetic particles 3a are introduced into the sample, which magnetic particles create a complex 3ac with the particles 3c. The particles 3a and 3c may form the complex in several different ways. The coating (e.g. antibody) of the magnetic particle 3a identifies the structures on the surface of the particles 3c or the same biological components as those that the particles 3c specifically bind onto their surface from the sample. The particles 3a form a complex 3ac together with the particles 3c, which enables the said complex to be handled with the magnetic tools according to the invention.

FIG. 13 shows non-magnetic and non-magnetisable particles 3c, which can be coated with a suitable special coating, such as e.g. antibodies, phage proteins or lectins. The particles 3c collect the desired biological components from the sample on their surface. One or several large-sized magnets 3b are inserted into the sample and a complex 3bc is formed in the sample. The complex 3bc may be formed in several different ways. The coating (e.g. antibody) of the magnetic particle 3b identifies the structures on the surface of the particles 3c or the same biological components as those that the particles 3c specifically bind on their surface from the sample. The particles 3b create a complex 3bc together with the particles 3c, which enables the said complex to be handled with the magnetic tools according to the invention.

In FIG. 14, both non-magnetic particles 3c and magnetic particles 3a have been introduced into the sample, which particles form complexes 3ac in the sample. When the magnet 3b is inserted into the sample, the complexes 3ac gather on the surface of the magnet 3b with the help of the magnet particles 3a. The end result is a complex 3abc, which can be handled by means of the magnetic tools according to the invention.

15 The Use of a Large Magnetic Object with Small Magnetic Particles and a Magnetic Tool The series of illustrations 15a-15c shows the use of a large magnetic object with small magnetic particles and a magnetic tool. FIG. 15a shows a large container 15a, which contains a sample 2 with magnetic particles 3a. One or several magnets 3b are inserted into the sample 2. In 15b, the magnet 3b has collected the magnetic particles 3a from the sample 2 on its surface and created a formed 3ab. A magnetic tool 7 according to the invention is introduced into the sample, which magnetic tool may in this case be, for example, a ferromagnetic object 7. The ferromagnetic object 7 may be suitably coated or surrounded with a changeable protective membrane. FIG. 15c shows a small-sized container 15b containing a solution 2, into which a complex 3ab has been transferred by means of the magnetic tool 7.

16 The Use of a Large Magnetic Object with Small Magnetic Particles and a Magnetic Tool

The series of illustrations 15a-15c shows the use of a large magnetic object with small magnetic particles and a magnetic tool. FIG. 16a shows the magnetic particles 3a contained in the sample 2 contained in the large-sized container 15a. The magnet 3b which is a fixed part of the magnetic tool 7 is introduced into the sample. In FIG. 16b, the magnet 3b has collected the magnetic particles 3a from the sample 2 onto its surface. In FIG. 16c, the complex 3ab has been transferred by means of the magnetic tool 7 away from the large container 15a into the solution 2 in the small container 15b. The magnet 3b may be of different shapes and sizes, and no other magnet is needed to connect it to the magnetic tool 7, but it can, for example, be set into the non-ferromagnetic frame of the tool. According to one preferred alternative, the magnetic particles 3a have already been attached to the magnet 3b prior to introducing the magnet 3b into the container 15a.

17-20 Lead-Through Structure with Places for Several Separate Magnetic Tools

Figure 18:
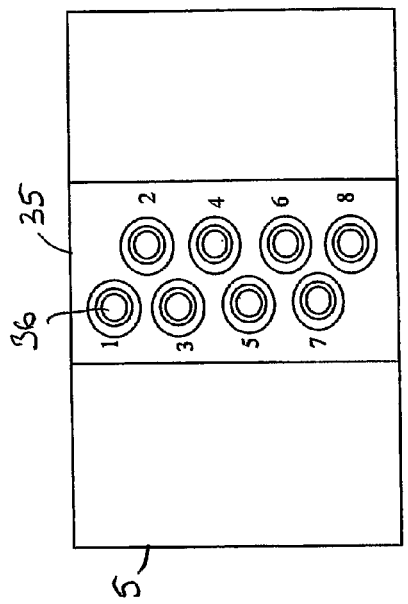
FIGS. 17-19 are schematic views of the lead-through structure of the enrichment unit from different directions.
Figure 17:
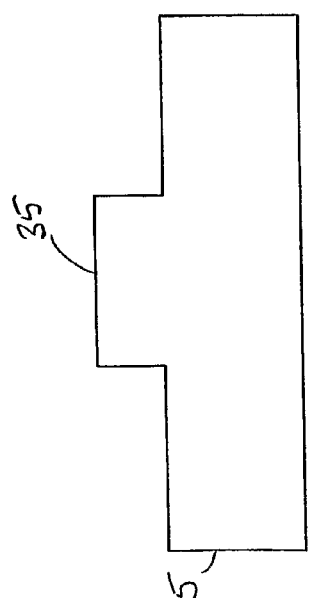
Figure 20:
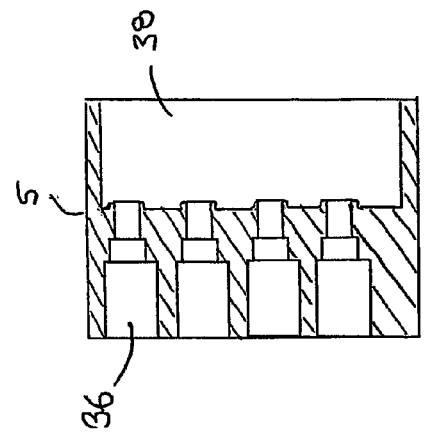
FIG. 20 is a sectional view of FIG. 19 along the line A-A.
Figure 19:
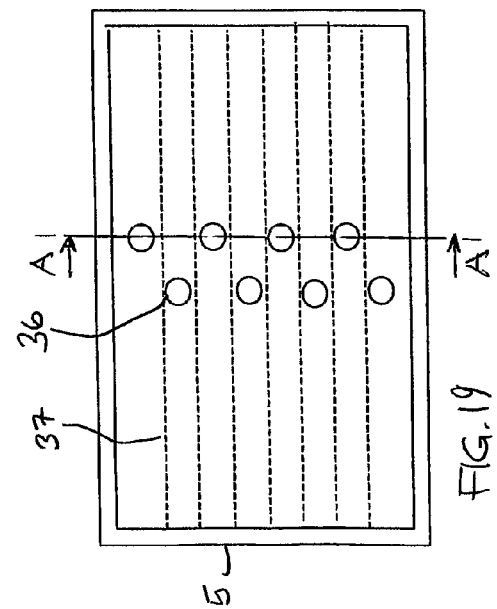

FIGS. 17-19 show, from different directions, the lead-through structure 5 of the enrichment unit according to the invention, which lead-through structure has places for several separate magnetic tools. FIG. 17 is a side view of the lead-through structure 5, wherein the ridge 35 represents the area onto which the magnetic tools 7 used in the enrichment unit according to the invention are placed. FIG. 18 is a top view of the lead-through structure 5. The ridge 35 of the lead-through structure 5 has numbered openings 36 for the magnetic tools 7. FIG. 19 is a bottom view of the lead-through structure 5. In the spaces between the openings 36 of the lead-through structure there may be various recesses or ridges 37 to separate the compartments of the sample container from one another. FIG. 20 shows a sectional view of the lead-through structure 5 in FIG. 19 along the line A-A at the level of the magnetic tool openings 36. FIG. 20 also shows the space of the sample container 38.

21-24 Cover and Sample Container with Places for Several Separate Magnetic Tools

Figure 21:
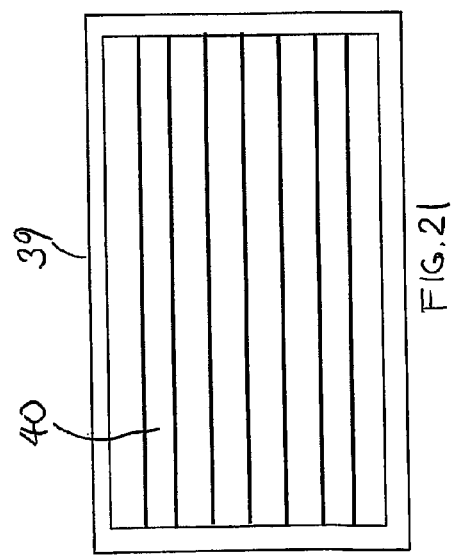
FIG. 21 is a top view of the sample container.

FIG. 21 is a top view of the sample container 39 with 8 sample compartments 40.

Figure 22:
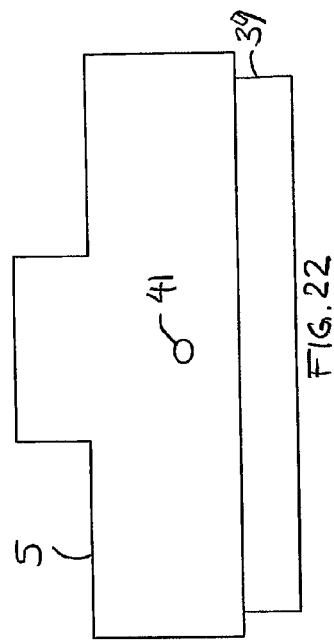
FIG. 22 is a schematic side view of the sample container and cover.

FIG. 22 is a side view of the lead-through structure 5 shown in FIG. 14 and the sample container 39 together, so that the lead-through structure 5 is placed on top of the sample container 39. The cover 5 has places for several separate magnetic tools 7. The lead-through structure 5 may be locked into the sample container 39 using various locking mechanisms 41.

Figure 23:
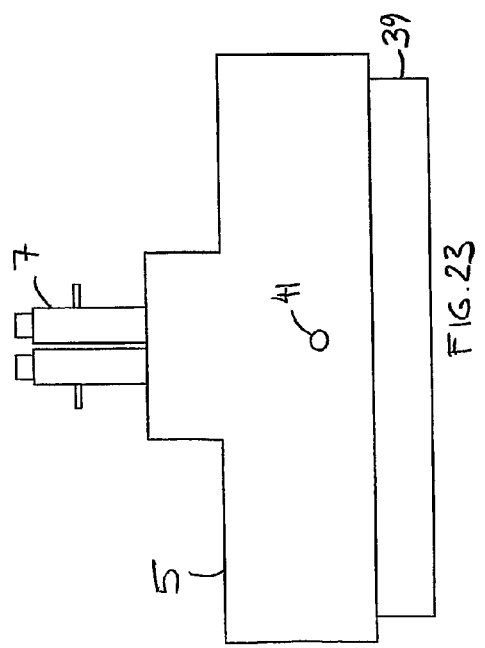
FIG. 23 shows the sample container and cover in FIG. 22, into which magnet tools have been inserted.

FIG. 23 is a side view of a situation where the magnetic tools 7 are arranged in connection with the lead-through structure 5 and the sample container 39. In this case, there is one magnetic tool 7 for each sample compartment 40 and the magnetic tools 7 rest on the lead-through structure 5.

Figure 24:
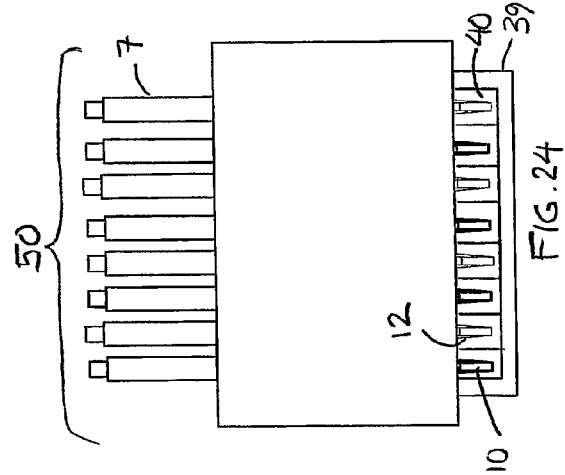
FIG. 24 is a schematic view of the sample container in a partly sectional view from one side and of the cover into which magnet tools have been inserted.

FIG. 24 shows the set of apparatuses of FIG. 23 seen from the other side and a partly sectional view of the sample container 39. FIG. 24 shows the lead-through structure 5 and the sample container 39 with all 8 magnetic tools placed on top of the lead-through structure 5. As FIG. 24 is a partly sectional view of the sample container 39, it shows the magnets 10, which are protected by the protective membrane 12 of the magnetic tools 7, which magnets collect particles from the sample compartments 40. The magnetic tools 7, the lead-through structure 5, the sample container 1 and the sample volumes to be used are all suitably dimensioned in relation to one another, so that the particles can be collected as efficiently as possible from the samples contained in the sample compartments 40.

25 Particle Transfer from the Surface of an Elastomeric Protective Membrane of the Magnetic Tool Directly onto the Culture Plate

Figure 25:
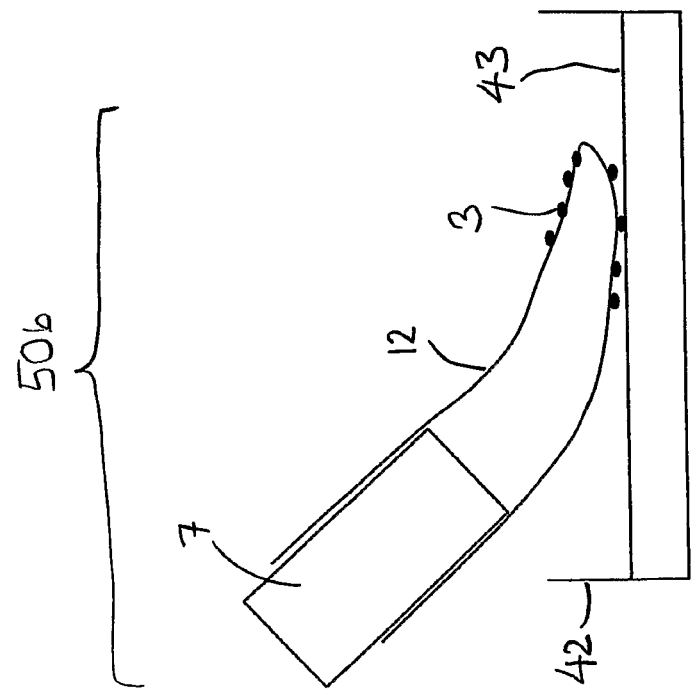
FIG. 25 shows the use of an elastomeric protective membrane for spreading the particles on the culture plate.

FIG. 25 shows the use of a protective membrane 12 made of elastomeric material to transfer the particles 3, e.g. onto the agar surface 43 of a culture plate 42. Using the method according to the invention, the particles 3 may have been first used to collect e.g. bacteria from the sample, after which the particles 3 and the bacteria on their surface can be transferred directly, on the protective membrane 12, onto the culture plate 42. The bacteria may then be grown on the culture plate for as long as desired. When the magnet of the magnetic tool 7 is switched off or moved suitably away form the proximity of the particles 3, the particles 3 may be released from the surface of the protective membrane 12. No solution is need for releasing the particles 3, but in the method according to the invention, the particles are released on the surface of the culture plate 42 by moving the protective membrane 12.

The elastomeric protective membrane 12 being of a very flexible and soft material, such as e.g. silicone rubber, the particles 3 may be released from the surface of the protective membrane 12 onto the culture plate 42 gently without damaging the agar surface 43. The elastomeric protective membrane 12 bends and conforms to the movements of the magnetic tool 7 on the surface of the culture plate 43 when releasing the particles from the surface of the protective membrane 12. If required, the protective membrane 12 may also be used for transferring the particles 3 from one culture plate to another or when switching the magnetic field on suitably on the inside of the protective membrane. The protective membrane 12 may be of different shapes and sizes and have special shapings as required.

26 Particle Transfer from the Surface of a Non-Elastomeric Protective Membrane of the Magnetic Tool Directly onto the Culture Plate

Figure 26:
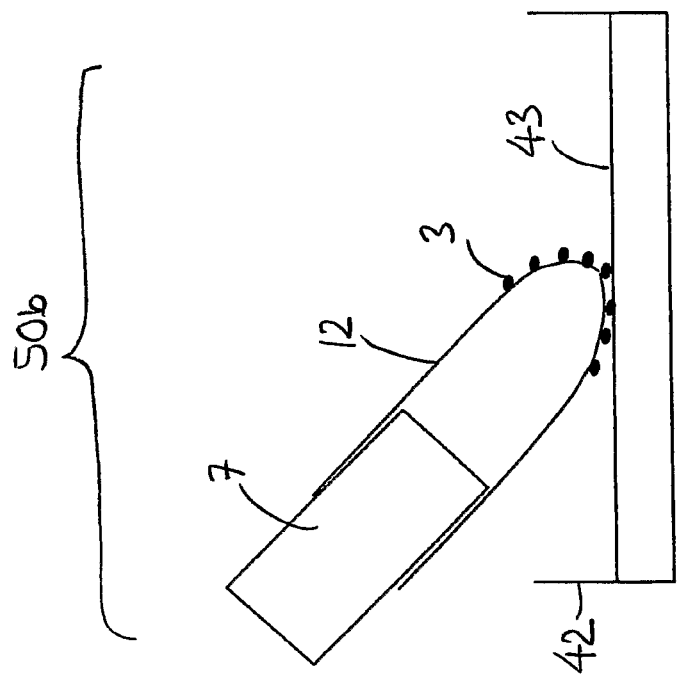
FIG. 26 shows the use of a non-elastomeric protective membrane for spreading the particles on the culture plate.

FIG. 26 shows the transfer of the particles 3 from the surface of the non-elastomeric protective membrane 12 of the magnetic tool 7 directly onto the culture plate 42. FIG. 26 shows particles 3 on the surface of the protective membrane 12 made of non-elastomeric material of the magnetic tool 7. The magnet of the magnetic tool 7 has been transferred away from the proximity of the particles 3, or the magnetic force has otherwise been switched off in the proximity of the particles 3. The particles 3 may be released onto different surfaces, such as e.g. the agar surface 43 of the culture plate 42. By moving the protective membrane 12 on the surface 43 of the culture plate 42, the particles can be released from the surface of the protective membrane 12. When using a protective membrane 12 made of non-elastomeric material for spreading the particles 3 on the surface, it is important to keep the protective membrane 12 at a suitable angle in relation to the surface and it is advisable to make the movements of the protective membrane on the surface gentle.

The set of apparatuses in FIG. 25 may be understood as being the part 50b of the set of enrichment apparatuses 50, so that it forms the latter part of the set of enrichment apparatuses 50 and, for example, the set of apparatuses of FIG. 1 comprises the first part 50a of the set of enrichment apparatuses 50. The set of apparatuses in FIG. 26 is an alternative to the set of apparatuses in FIG. 25.

According to the invention, such an enrichment or concentration apparatus can concentrate the large sample volume 1 in FIG. 1 with the help of the magnetic tool 7 directly on the surface 43 of the culture plate 42 shown in FIG. 25 or FIG. 26, to a very small volume. Thereby, a very high concentration or enrichment rate is achieved in a single operation.

27-29 Protective Membrane End Structure

Figure 29:
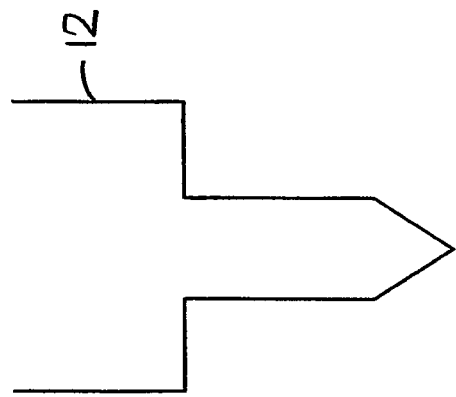
FIGS. 27-29 are schematic side views of different end structures of the protective membrane.
Figure 28:
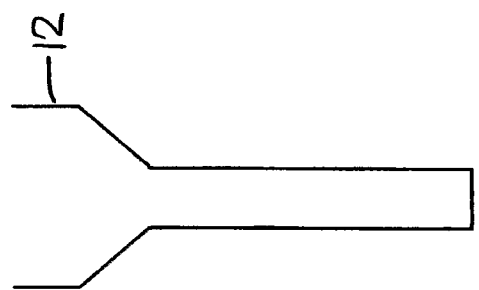
Figure 27:
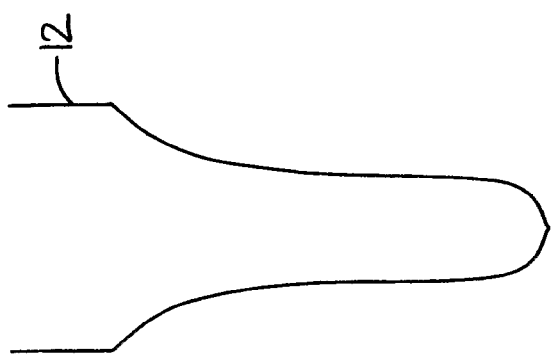

FIGS. 27-29 show different end designs for the protective membrane 12. FIG. 27 shows a round end of the protective membrane 12. In FIG. 28, the end of the protective membrane 12 is flat and in FIG. 29, the end of the protective membrane 12 is pointed. The magnets corresponding to these illustrations inside the protective membrane 12 may also be shaped to correspond to the shapes created in the protective membrane 12. All the cases shown in these illustrations include an elongated and end-shaped portion to assist the concentration of particles into different small container types and/or the spreading of the particles on different surfaces.

30 Protective Membrane End

Figure 30C:
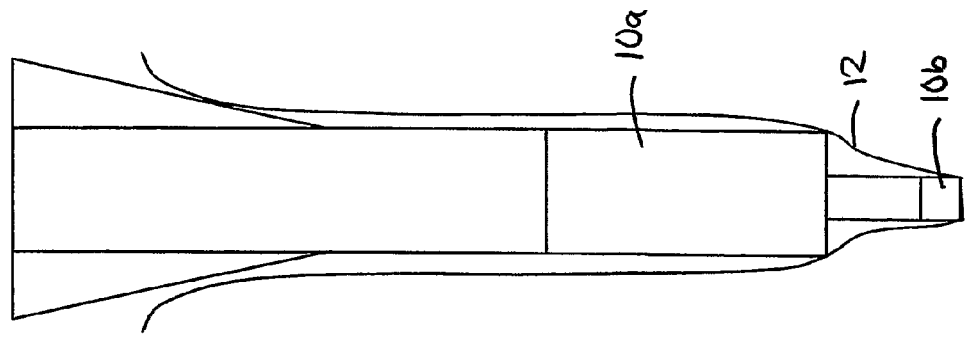
FIGS. 30a-30c are schematic side views showing the functioning of the end structure of the magnetic tool's elastomeric protective membrane.
Figure 30B:
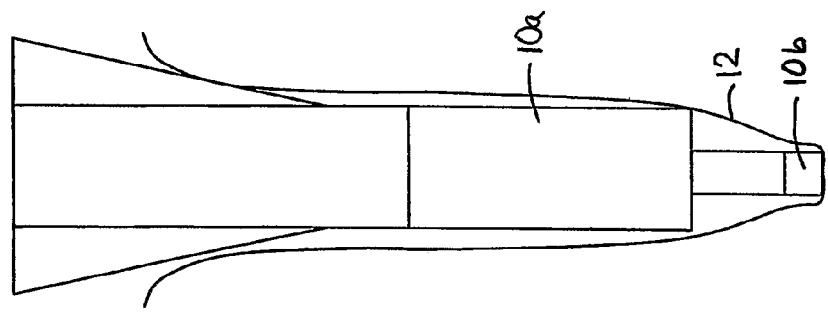
Figure 30A:
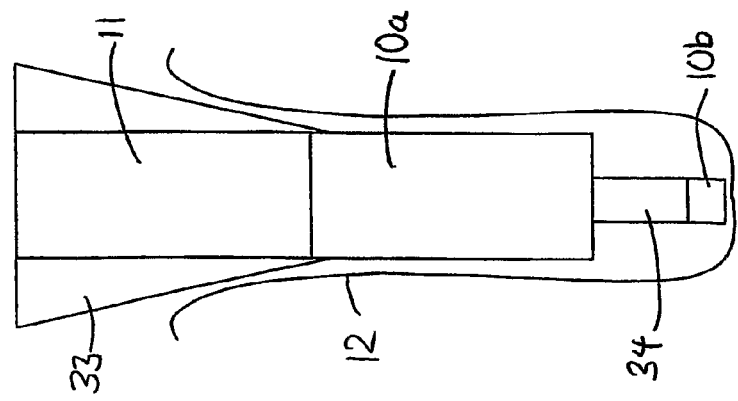

The series of illustrations 30a-30c shows the operation of the end of the protective membrane 12 in different situations. FIG. 30a shows the magnets 10a and 10b located inside the elastomeric protective membrane 12 and the protective membrane 12, which is in contact with the frame structure 33 of the magnetic means. The magnets 10*a* and 10*b* are moved by means of the rod 11 and the magnet 10*b* has been connected to the magnet 10*a* by means of the rod 34. In FIG. 30*a*, the end structure of the protective membrane 12 is not particularly narrow or advantageous for concentrating particles into small containers. In FIG. 30*b*, the rod 11 has been used to move the magnet 10*b* against the protective membrane 12 and to stretch the protective membrane 12. In FIG. 30*c*, the magnet 10*b* has been used to stretch the protective membrane 12 further, and, as shown by the illustration, the structure of the protective membrane 12 conforms to the shape of the magnet 10*b*. The elastomeric protective membrane may be used to realise solutions that require a small size and desired shape of the protective membrane for concentrating the particles.

Example 1

Use of the Method According to the Invention for Determining *Salmonella* Bacteria from Food Samples The samples (25 g or 25 ml) were homogenised in 225 ml of fresh growth medium (buffered peptone water) in stomacher bags with filters (BagPage® 400 ml, Interscience). The samples were homogenised in the stomacher bags, after which the orifices of the stomacher bags were closed and the bags positioned in a stand (Wire basket, Bochem) were placed in a shaker located in an incubator (Unimax 1010, Heidolph). The stomacher bags were agitated for 5 h 30 min (300 rpm, +41° C.±1.0° C.).

The sample container cover was placed on top of the sample container (product number, Innovative Microplate Inc.). The sample container has compartments for 8 samples and the sample container cover, correspondingly, has places (openings) for eight PickPen 1-M (Bio-Nobile Oy) magnetic tools. 20 μl of anti-*salmonella* antibody-coated magnetic particles were pipetted through the openings in the sample container cover into the compartments in the sample container.

The laboratory shaker located in the incubator was stopped after the stomacher bags had been agitated for 5 h 30 min. The stand in which the stomacher bags were placed was removed from the shaker and placed on the laboratory work table. The stomacher bags were opened and a 10 ml sample was taken from each of them and dosed through the openings in the sample container cover into the compartments of the sample container. One 10 ml sample was dosed into each compartment of the sample container. After this, the sample container covered with the sample container cover was placed in the laboratory shaker located in the incubator. The samples were incubated in the mixture with the magnetic particles for 50 minutes (300 rpm, +41° C.±1.0° C.). The magnetic particles contained in the compartments of the sample container at this stage collected the *Salmonella* bacteria present in the sample on their surface.

After incubation, the shaker was stopped and the PickPen 1-M tools, provided with protective membranes of silicone rubber to protect the magnet, were placed on top of the sample container cover. The magnet of the PickPen 1-M was locked into the magnetic particle collecting position, i.e. the magnet was outside. After all the PickPen 1-M tools had been placed in their positions, the agitation of the samples was continued with the same settings for 10 minutes. During agitation, the magnetic field inside the silicone tip of the PickPen 1-M caused the magnetic particles to gather around the tip.

The shaker was stopped and the sample container, sample container cover and PickPen 1-M were moved, as a single assembly, away from the shaker and placed on the laboratory table. After this, the PickPen 1-M magnetic tools were lifted from the top of the sample container cover one at a time. Two *Salmonella*-selective culture plates had been provided for each individual sample: Xylose lysine deoxycholate (XLD) and Rambach plates. The magnetic particles collected on the silicone rubber protective membrane of the PickPen 1-M, to which particles the *Salmonella* bacteria were bound, were spread directly on the culture plates by means of the silicone tip. Immediately before spreading the magnetic particles on the surface of the culture plates, the magnet of the PickPen 1-M was moved into the magnetic particle release position, i.e. the magnet was locked into its upper position. There was no longer any magnetic field exerted on the magnetic particles, so that these could be mechanically spread on the surface of the culture plates. By turning the silicone tip suitably, the magnetic particles could be distributed on two different culture plates. Silicone rubber is a bending and flexible material which does not damage the surface of the agarose plates but functions as an excellent means for spreading the magnetic particles and the *Salmonella* bacteria bound to them.

Example 2

Plating Method for the Magnetic Particle-*Salmonella* Complex

The plating of the magnetic particle-*Salmonella* complex is performed so that the method comprises the following stages:

1. 150 μl of PBS (pH 7.4) 0.05% Tween 20 solution is pipetted onto two *Salmonella*-selective agar plates: XLD and Rambach-agar plates. The purpose of the PBS solution is to facilitate the spreading of the magnetic particles on the surface of the plates.
2. The PickPen 1-M is gently lifted off the PickPen-cover-container complex without touching the walls of the PickPen cover. The magnet of the PickPen 1-M is released into the upper position. Releasing the magnet eliminates the magnetic field from around the silicone tip of the PickPen 1-M, in which case a magnetic field is no longer exerted on the magnetic particles. This makes it possible to transfer the magnetic particles e.g. onto a suitable culture plate by means of the soft and flexible silicone tip of the PickPen 1-M.
3. The magnetic particles gathered in the end of the PickPen are distributed over two plates (XLD and Rambach) using the flexible silicone tip of the PickPen. The magnetic particles form two separate pellets on the surface of the silicone tip of the PickPen 1-M, as the PickPen 1-M uses a NeFeB permanent magnet magnetised in a direction perpendicular to the longitudinal axis. This is an ideal situation when the magnetic particles collected from the sample are to be distributed as accurately and simply as possible over two selective culture plates.

4. The magnetic particles are mixed on the XLD plates into the PBS solution and the solution is spread evenly on one half of the plate using the silicone tip of the PickPen 1-M. The operation is continued by spreading the magnetic particles on the other clean half of the plate.
5. The magnetic particles are spread as described in paragraph 4 on the Rambach plate using the same PickPen 1-M silicone tip. Finally, the tip is removed from the PickPen 1-M and the plates are placed in an incubator at +37° C.±1° C. for 16 hours. The culture plates are then analysed and the *Salmonella* colonies counted.

method complying with the ISO 6579 standard. The results in Table 1 show that similar results were obtained with the method according to the invention as with the ISO method in force. Obtaining a positive or negative result by the method developed took only 22.5 hours, while obtaining the same result by the ISO method took 58-74, hours depending on the incubation times.

TABLE 1

Comparison of the method according to the invention and the ISO 6579 method using food samples with added *Salmonella* bacteria.

| | | | Method according to the invention Total time = 22.5 h | | | ISO 6579 Total time = 58-74 h | | |
|---|---|---|---|---|---|---|---|---|
| | | | | | | RVS XLD | MKTTN XLD | |
| Sample | *Salmonella* strain | Cells/25 g | XLD | Rambach | Result | Rambach | Rambach | Result |
| Chicken and vegetables | *S. Blockley* | 69.7 | + | + | + | + | + | + |
| | | 232.5 | + | + | + | + | + | + |
| Cheese potato gratin | | 69.7 | + | + | + | + | + | + |
| | | 232.5 | + | + | + | + | + | + |
| Ham | *S. Infantis* | 16.1 | + | + | + | + | + | + |
| | | 53.6 | + | + | + | + | + | + |
| Mashed chicken and beans | | 16.1 | + | + | + | + | + | + |
| | | 53.6 | + | + | + | + | + | + |
| Tomato pepperoni pasta | *S. Enteritidis* | 8 | + | + | + | + | + | + |
| | | 26.8 | + | + | + | + | + | + |
| Fish in lemon sauce | | 8 | + | + | + | + | + | + |
| | | 26.8. | + | + | + | + | + | + |
| Salmon (Atlanti) | *S. Virchow* | 4. | − | − | − | − | − | − |
| | | — | − | − | − | − | − | − |
| Fish | | 1.3 | − | − | − | − | − | − |
| | | 4.3 | + | + | + | + | + | + |
| Mussel | *S. Senftenberg* | 5 | + | + | + | + | + | + |
| | | 16.8 | + | + | + | + | + | + |
| Smoked salmon | | 5 | + | + | + | + | + | + |
| | | 16.8 | + | + | + | + | + | + |
| Crab | *S. Montévidéo* | 0.3 | − | − | − | − | − | − |
| | | 1.1 | − | − | − | − | − | − |
| Anchovy mousse (anchovy + cream) | | 0.3 | − | − | − | − | − | − |
| | | 1.1 | − | − | − | − | − | − |

XLD = Xylose Lysine Decarboxylase agar
Rambach = Rambach agar
RVS = Rappaport Vassiliadis broth
MKTTN = Muller-Kauffmann Tetrathionate Novobiocin broth
ISO 6579:2002 = Microbiology of food and animal feeding stuffs - Horizontal method for the detection of *Salmonella* spp Example 3

Comparison of the Enrichment Method According to the Invention and the Method Complying with the ISO 6579 Standard The method developed was compared against the ISO standard in force in the industry (ISO 6579: 2002 Microbiology of food and animal feeding stuffs. Horizontal method for the detection of *Salmonella* spp.). The ISO 6579 standard defines the procedures to be applied for testing foodstuffs and animal feeding stuffs for Salmonellae. Different amounts of *Salmonella* bacteria were added to the food samples (25 g) after the addition of buffered peptone water.
Table 1:
Results Obtained in Example 3
Table 1 shows the results obtained in example 3 and compares the enrichment method according to the invention to the

LIST OF REFERENCE NUMBERS

1 Bag
2 Liquid sample
3 Particle
4 Stand
5 Lead-through structure
6 Locking system
7 Magnetic tool
8 Sealer
9 Structure
10 Magnet
11 Rod
12 Protective membrane
13 Mechanism
14 Orifice
15 Tube
16 Solution level
17 Solution
18 Apparatus
19 Connector
20 Worktop
21 Bushing-aeration unit
22 Bubbling hole 23 Counter-connector
24 Particle washing and concentration unit
25 Opening
26 Container
27 Bushing
28 Rod
29 Arm
30 Track
31 Space between container and protective membrane
32 Stand assembly
33 Frame structure
34 Rod
35 Ridge
36 Opening
37 Recess or ridge
38 Space of the sample container
39 Sample container
40 Sample compartment
41 Locking mechanism
42 Culture plate
43 Agar surface
44 Wall
50 Enrichment unit
50a First part of the enrichment unit
50b Latter part of the enrichment unit

The invention claimed is:

1. A biological component enrichment unit (50) for the isolation, purification or determination of a biological component using particles (3) or other solid phases contained in a liquid sample (2) comprising:
   (a) a magnetic tool (7);
   (b) a washing and concentration unit (15,24) or culture plate (43);
   (c) at least one sample container (1), wherein the at least one sample container is a sample bag (1) selected from the group consisting of: a food stomacher bag, water sample bag, and blood bag, wherein the at least one sample container is for holding a liquid sample (2) whose volume is essentially greater than that of the containers of the washing and concentration unit (15, 24),
   (d) a lead-through structure (5) comprising a bushing (21, 27), wherein the bushing comprises one or several parts or a cover having one or several openings (25, 36), wherein the lead-through structure is fastenable to the sample bag; and
   (e) a stand (4), which is connected to the lead-through structure (5), wherein the stand (4) is separate from the sample bag (1).

2. The enrichment unit according to claim 1, wherein the lead-through structure (5) comprises one or several openings (25, 36) for introducing a sample (2), a solid phase, different solutions or particulate materials into the at least one sample container (1) or for removing them from the at least one sample container.

3. The enrichment unit according to claim 1, wherein the openings (25, 36) of the lead-through structure (5) receives the magnetic tool (7).

4. The enrichment unit according to claim 1, wherein the lead-through structure (5) is closed or sealed with a tool, plug, membrane, filter or other suitable structure (8), which prevents or reduces splashes, evaporation and cross contaminations.

5. The enrichment unit according to claim 1, wherein the lead-through structure (4) is locked into the sample container (1) with a locking mechanism (41).

6. The enrichment unit according to claim 1, wherein the single lead-through structure (5) comprises openings giving access alternatively to at least two sample containers (1).

7. The enrichment unit according to claim 1, wherein the enrichment unit comprises a support structure (9) for supporting the bag (1) or squeezing or moving the bag by agitation from outside has been arranged in connection with the lead-through structure (5).

8. The enrichment unit according to claim 1, wherein the magnetic tool (7) has been arranged in connection with the lead-through structure (5).

9. The enrichment unit according to claim 1, wherein the biological component collected from the sample container (1) using the washing and concentration unit (15, 24) is enriched to a smaller volume or on the surface (43) of a culture plate.

10. A biological component enrichment unit (50) for the isolation, purification or determination of a biological component using particles (3) or other solid phases contained in a liquid sample (2) comprising:
    (a) a magnetic tool (7);
    (b) at least one sample container (1), wherein the at least one sample container is a sample bag (1) selected from the group consisting of: a food stomacher bag, water sample bag, and blood bag, wherein the at least one sample container is for holding a liquid sample (2);
    (c) a lead-through structure (5) comprising a bushing (21, 27), wherein the bushing comprises one or several parts or a cover having one or several openings (25, 36), wherein the lead-through structure is fastenable to the sample bag; and
    (d) a stand (4), which is connected to the lead-through structure (5), wherein the stand (4) is separate from the sample bag (1).

11. The enrichment unit according to claim 10, wherein the lead-through structure (5) comprises one or several openings (25, 36) for introducing a sample (2), a solid phase, different solutions or particulate materials into the at least one sample container (1) or for removing them from the at least one sample container.

12. The enrichment unit according to claim 10, wherein the openings (25, 36) of the lead-through structure (5) receives the magnetic tool (7).

13. The enrichment unit according to claim 10, wherein the lead-through structure (5) is closed or sealed with a tool, plug, membrane, filter or other suitable structure (8), which prevents or reduces splashes, evaporation and cross contaminations.

14. The enrichment unit according to claim 10, wherein the lead-through structure (4) is locked into the sample container (1) with a locking mechanism (41).

15. The enrichment unit according to claim 10, wherein the single lead-through structure (5) comprises openings giving access alternatively to at least two sample containers (1).

16. The enrichment unit according to claim 10, wherein the enrichment unit comprises a support structure (9) for supporting the bag (1) or squeezing or moving the bag by agitation from outside has been arranged in connection with the lead-through structure (5).

17. The enrichment unit according to claim 10, wherein the magnetic tool (7) has been arranged in connection with the lead-through structure (5).

18. The enrichment unit according to claim 10, wherein the biological component collected from the sample container (1) using a washing and concentration unit (15, 24) is enriched to a smaller volume or on the surface (43) of a culture plate.

* * * * *